(12) United States Patent
Ablett

(10) Patent No.: US 9,974,820 B2
(45) Date of Patent: *May 22, 2018

(54) METHOD AND APPARATUS FOR SMOKE-INFUSING PROTEINACEOUS FOODS AND SMOKED-INFUSED SUCH PROTEINACEOUS FOOD PRODUCT SO-OBTAINED

(71) Applicant: Richard Ablett, Charlottetown (CA)

(72) Inventor: Richard Ablett, Charlottetown (CA)

(73) Assignee: CRUSTOCEAN TECHNOLOGIES LIMITED, Charlottetown (CA)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/049,694

(22) Filed: Feb. 22, 2016

(65) Prior Publication Data

US 2016/0193266 A1 Jul. 7, 2016

Related U.S. Application Data

(60) Continuation-in-part of application No. 14/070,680, filed on Nov. 4, 2013, now Pat. No. 9,277,757, which (Continued)

(30) Foreign Application Priority Data

Feb. 18, 2009 (CA) ..................... 2655426

(51) Int. Cl.
*A23C 19/14* (2006.01)
*A61K 36/185* (2006.01)
(Continued)

(52) U.S. Cl.
CPC ............. *A61K 36/185* (2013.01); *A01J 27/00* (2013.01); *A23B 4/052* (2013.01);
(Continued)

(58) Field of Classification Search
CPC ........ A01J 25/007–25/008; A01J 25/00; A01J 25/162; A01J 27/00; A01J 27/02;
(Continued)

(56) References Cited

U.S. PATENT DOCUMENTS 2,266,131 A * 12/1941 Thon ..................... A23B 4/052
126/59.5
2,920,968 A 1/1960 Grandy
(Continued)

FOREIGN PATENT DOCUMENTS

NL 1018855 C2 * 3/2003 ........... A23C 19/054

OTHER PUBLICATIONS

Smoking Food NPL, www.bhg.com/recipes/grilling/basics/how-to-smoke-food/printPage , 2008.*

*Primary Examiner* — Drew E Becker
(74) *Attorney, Agent, or Firm* — Nath, Goldberg & Meyer; Jerald L. Meyer

(57) ABSTRACT

A method of smoke-infusing proteinaceous foods comprises the following sequential steps: a) enclosing the proteinaceous foods in a vacuum-treating zone; b) introducing smoke directly or indirectly from a smoke generation zone into the vacuum-treating zone; c) subjecting the proteinaceous foods to vacuum purging at a negative pressure in the vacuum-treating zone, thereby infusing smoke into the proteinaceous foods; d) repeating the steps of introducing smoke directly or indirectly from the smoke generation zone into the vacuum-treating zone; subjecting the proteinaceous foods to vacuum purging at a negative pressure in the vacuum-treating zone at least fifty times in pulsed sequences of smoke introduction stage/vacuum purging stage/vacuum release stage for the efficient infusion of smoke into the proteinaceous foods; and e) a post-chill resting cycle of the smoke-infused proteinaceous foods at a suitable temperature and for a suitable period of time. An optional modification (Continued)

to the smoke-infusing process is the addition of *Cannabis* plant material in order to enable the deposition of *Cannabis*-derived compounds on the surface of the smoke-infused food.

25 Claims, 5 Drawing Sheets

Related U.S. Application Data is a division of application No. 13/059,163, filed as application No. PCT/CA2010/000222 on Feb. 18, 2010, now Pat. No. 8,574,652.

(51) Int. Cl.

| | | |
|---|---|---|
| *A61K 9/00* | (2006.01) | |
| *A23C 19/10* | (2006.01) | |
| *A23L 3/3418* | (2006.01) | |
| *A01J 27/00* | (2006.01) | |
| *A23B 4/052* | (2006.01) | |
| *A23L 27/27* | (2016.01) | |
| *B65B 25/00* | (2006.01) | |
| *B65B 25/22* | (2006.01) | |
| *A23C 19/09* | (2006.01) | |
| *B65B 31/02* | (2006.01) | |

(52) U.S. Cl.
CPC .......... *A23C 19/0925* (2013.01); *A23C 19/10* (2013.01); *A23C 19/14* (2013.01); *A23L 3/3418* (2013.01); *A23L 27/27* (2016.08); *A61K 9/0056* (2013.01); *B65B 25/001* (2013.01); *B65B 25/22* (2013.01); *A23C 2250/35* (2013.01); *B65B 31/024* (2013.01)

(58) Field of Classification Search
CPC ........... A23C 1/14; A23C 3/08; A23C 19/097; A23C 19/10; A23C 2250/35; A23B 4/044–4/056; A23B 4/10; A23L 3/34; A23L 3/3445
USPC .................................................. 426/314, 582
See application file for complete search history.

(56) References Cited

U.S. PATENT DOCUMENTS

| | | | |
|---|---|---|---|
| 3,671,272 A | 6/1972 | Mixon | |
| 3,896,242 A | 7/1975 | Moore | |
| 4,946,326 A | 8/1990 | Schvester et al. | |
| 5,368,872 A | 11/1994 | Davis, Jr. | |
| 5,484,619 A | 1/1996 | Yamaoka et al. | |
| 5,543,513 A | 8/1996 | Mandai et al. | |
| 5,967,027 A * | 10/1999 | Higashimoto | A23B 4/044 |
| | | | 126/21 A |
| 6,440,484 B1 | 8/2002 | Tanaka et al. | |
| 6,579,549 B1 | 6/2003 | Thrasher et al. | |
| 8,574,652 B2 * | 11/2013 | Ablett | A23B 4/052 |
| | | | 426/129 |
| 9,277,757 B2 * | 3/2016 | Ablett | A23B 4/052 |
| 2001/0046539 A1 | 11/2001 | Turner et al. | |
| 2004/0213876 A1 | 10/2004 | Olson et al. | |
| 2004/0247769 A1 * | 12/2004 | Victoria | A23L 13/03 |
| | | | 426/641 |
| 2007/0028782 A1 | 2/2007 | Chiu | |
| 2008/0307978 A1 * | 12/2008 | Bassoli | A23L 5/13 |
| | | | 99/474 |
| 2011/0247505 A1 * | 10/2011 | Davis | A23B 4/052 |
| | | | 99/472 |
| 2012/0040061 A1 * | 2/2012 | Caputi | A23B 4/044 |
| | | | 426/235 |
| 2012/0046351 A1 * | 2/2012 | Hospodor | A23G 1/42 |
| | | | 514/454 |
| 2013/0040061 A1 | 2/2013 | Lowrance et al. | |
| 2015/0342204 A1 * | 12/2015 | Deumier | A23L 3/40 |
| | | | 34/412 |

* cited by examiner

METHOD AND APPARATUS FOR SMOKE-INFUSING PROTEINACEOUS FOODS AND SMOKED-INFUSED SUCH PROTEINACEOUS FOOD PRODUCT SO-OBTAINED

This is a Continuation-in-Part application of U.S. application Ser. No. 14/070,680, filed Nov. 4, 2013, which is a divisional application of U.S. application Ser. No. 13/059,163, filed Feb. 15, 2011, now U.S. Pat. No. 8,574,652, which is a National Phase Application filed under 35 USC 371 of International Application Number PCT/CA2010/000222, filed Feb. 18, 2010, an application which claims foreign priority benefits under 35 USC 119 of Canadian Patent Application Number 2,655,426, filed Feb. 18, 2009, the entire content of each of which is hereby incorporated by reference in their entirety.

TECHNICAL FIELD

This invention relates to the field of smoke-infusing proteinaceous foods, e.g., cheeses, crustaceans, bivalve mollusks, gastropod mollusks, fish, meats and poultry and to the smoked-infused such proteinaceous foods so-obtained.

BACKGROUND

The preservation of the above-identified proteinaceous foods, e.g., cheeses, crustaceans, bivalve mollusks, gastropod mollusks, fish, meats and poultry has been a major concern for humanity, and the following is a summary of the problems which have been encountered in the preservation of the above-identified proteinaceous foods.

Dating back thousands of years, before the invention of refrigeration, freezing and canning processes, various proteinaceous foods, e.g., cheeses, crustaceans, bivalve mollusks, gastropod mollusks, fish, meats and poultry, were cured by natural smoke. Historically, such proteinaceous foods have been smoked at atmospheric pressures and varying temperature ranges over long periods of time.

Smoke curing is typically done in one of two ways: namely cold-smoking; and hot smoking. The cold smoking method particularly where the proteinaceous foods products are cheeses can take up to one month depending on the cheese variety. The cold smoking process smokes proteinaceous food materials, e.g. cheese at between 4° C. to 28° C. The cold smoking method is a less stringent method and will assist in keeping proteinaceous food materials, e.g. cheese moist and acceptable.

Hot smoke can partially or completely cook, dry, and dehydrate foodstuffs and thus is not deemed to be suitable for cheeses and some other foods, by treating them at temperatures ranging from about 60° C. to about 75° C. Obviously, this should not apply to certain food categories, e.g. cheeses. Components of the smoke emitted from various types of fuel will enhance the taste and preserve the color of the food. However, it was found that smoking and cooking crustaceans, meat and poultry under pressure imparted more smoke flavor thereto tended to cause the crustaceans, meat and poultry to retain additional moisture, and caused the crustaceans, meat and poultry to be more tender as compared to meat smoked at atmospheric pressure.

Thus, with respect to cold-smoking and hot smoking, the combinations and variations in temperature from about 4° C. to about 70° C., fuel types, humidity, circulation and exposure times are great.

Historically such proteinaceous foods have been smoked at atmospheric pressures and varying temperature ranges over relatively long periods of time. It was later found that the time required to smoke such proteinaceous foods adequately could be reduced if the smoking method could be performed under pressure. It was also found that smoking such proteinaceous foods under pressure imparted more smoke flavor to the food and tended to cause such proteinaceous foods to retain additional moisture. It was then later found that the time required to smoke such proteinaceous foods adequately could be reduced if the smoking and cooking processes could be performed in combination and under pressure.

Natural smoke can preserve the nutritional components and wholesomeness of dairy products while at the same time retarding spoilage. Smoked cheese, such as smoked cheddar cheese, smoked ham and smoked turkey breast are some examples of popular foods treated by smoke.

Another method of "curing" used in less expensive cheeses is to use liquid smoke flavoring to give the cheese the outside appearance of having been smoked in the more traditional manner.

Smoked cheese is any cheese that has been specifically treated by smoke curing. It typically has a yellowish-brown outer "coating", which is a result of this curing process. Furthermore, a common factor of the known smoking processes is that the total smoking time for cheese, smoked by method of liquid smoke, is comparatively long.

In the examples given above, the result has been a smoke-flavored food. Thus, the known processes are not completely satisfactory as regards the uniformity, the color quality and color stability and occasionally as regards their taste especially for cheeses. In many smoking methods, where separate heating surfaces are arranged in the path of the circulated treating medium (generally predominantly air), these are susceptible to contamination, wear and tear and faults.

In the field of processing of hard and soft shelled crustaceans, e.g., lobsters or crabs or shrimp, the processors have for many years used post-harvest stabilization as fresh chilled or frozen distribution methods. More typically, the processors subjected such lobsters or crabs or shrimp to methods of cooking then freezing whole and typically as frozen-in-brine packaging (e.g. known popularly in lobster processing as "popsicle pack") or by separating the cooked meat of such lobsters or crabs or shrimp from the shell and marketing such meat of such lobsters or crabs or shrimp as frozen vacuum-pack or canned products.

These lobster or crab or shrimp processing industries are traditional in their approach and these typical processing techniques are associated with a necessity to handle unpredictable catches and large seasonal volumes of raw such lobsters or crabs or shrimp for which there is a need to stabilize such lobsters or crabs quickly and with simplicity. These approaches do not necessarily attend the changing demands of modern consumers.

In recent years, these lobster or crab or shrimp or even the oyster processing industries have responded to consumer demand for fresh lobsters or crabs or shrimp by adopting new methods of processing which include the use of the separation of the raw meat from the shells of lobsters or crabs or shrimp and subsequent rapid freezing of such separated raw meat. These new methods include the use of freeze-thaw separation techniques as well as the use of applied high hydrostatic pressure which has been shown to effect release of raw meat from the shell material of lobsters or crabs or shrimp. Extracted raw meat of lobsters or crabs is then frozen and distributed for subsequent thawing and cooking.

Heretofore, packaging of such lobsters or crabs or shrimp in buyer-friendly containers having a good visibility of such has been virtually unknown as the shells of such lobsters or crabs, by virtue of their shape and their sharp appendages, made it inappropriate to vacuum seal the lobster or crab product in marketable packaging for retail use.

Other operators in these lobster or crab or shrimp processing industries are involved in post-harvest holding and live marketing of lobsters or crabs. These operators occupy a market niche (e.g. restaurant and supermarket trade) which is typically high priced and not available to the traditional cooked frozen product processors.

In the field of the sale of bivalve mollusks, e.g., oysters and clams and mussels and gastropod mollusks, e.g., abalone, it is known that bivalve and gastropod mollusk processors have sold freshly-caught oysters, mussels, clams and abalone, and for many years, have also utilized post-harvest stabilization of such bivalve and gastropod mollusks, by cooking such oysters, clams, mussels and abalone and have marketed the so-cooked products by fresh-chilled and frozen distribution. More typically, the mollusk processors subjected the so-cooked meat of such oysters, clams, mussels and abalone to methods of chilled shucked raw and cooked meat and individually quick frozen (e.g. known as "IQF") techniques, or, by separating the raw or so-cooked meat of such oysters, clams, mussels and abalone from the shell and marketing such raw or so-cooked meat as chilled pack, frozen vacuum-pack or further processed canned products. These bivalve mollusk and gastropod mollusk processing industries are generally not capable of handling unpredictable catches and large seasonal volumes of raw material for which there is a need to stabilize the bivalve or gastropod mollusk product quickly and with simplicity.

In recent years, this particular bivalve mollusk processing industry has responded to consumer demand for fresh oysters by adopting new methods of processing which include the use of raw meat separation from the shell of the oysters and subsequent rapid freezing These new methods include the use of freeze-thaw separation techniques as well as the use of applied high hydrostatic pressure which has been shown to effect both contaminant microbial destruction and permit ease of raw meat release from the retaining shell material. Extracted raw oyster meat is then either sold chilled raw or frozen raw and distributed for subsequent thawing and cooking.

The preservation of fish has been a major concern for fishermen and fish processors for centuries. Originally, fish were salted and/or dried to preserve fish. Historically, fish have been smoked at atmospheric pressures and varying temperature range over long periods of time. Smoking of fish has been one of the major forms of fish preservation for centuries. Such smoking, however, can also serve to cook the fish while imparting the smoke flavor. It was later found that the time required to smoke and cook the fish adequately could be reduced if the smoking and cooking processes could be performed in combination and under pressure. It was also found that smoking and cooking fish under pressure imparted more smoke flavor to the fish and tended to cause the fish to retain additional moisture as compared to meat smoked at atmospheric pressure.

Smoking involves the burning of organic substances, such as wood, to produce a complex mix of over 400 separate chemical compounds. These compounds, when continually exposed to fish flesh, are absorbed into the fish over time and impart a smoke flavor to the fish. The smoke compounds act as a natural "bacteriostat" and greatly increase the refrigerated shelf life of the fish (up to three times the un-smoked shelf life). It is believed that smoking of fish increases the shelf life by killing a majority of the bacteria initially present, and then creating an acidic microenvironment that slows the growth of bacteria over time in refrigerated conditions. Demand for smoked fish has been significant for many years and is continuing to grow.

It is well-known that raw meat of tuna and other fish becomes oxidized in a very short time, with attendant blackening and deterioration. This oxidation proceeds even in the meat frozen at approximately −20° C., the temperature used in ordinary freezing. Therefore, such fish is usually frozen, and kept, at lower temperatures. This is the reason why the transportation and preservation of fish caught in deep-sea areas and territorial waters of foreign countries are very costly. The use of air freight, in preference to transport on ships during which stable temperature control is difficult, adds further to the transportation cost of such fish. It has long been desired to establish some inexpensive method to transport and preserve fish without diminishing or spoiling flavor in a condition similar to that attained by ordinary freezing or cold-storage.

In addition to smoking meats under pressure, it has been found that smoking and cooking meats and poultry at a pressure less than the surrounding atmospheric pressure draws moisture from the meats and poultry and helps to more quickly preserve the foods. For example, meat jerky smoked at less than atmospheric pressure cures more quickly and with a more desirable texture than does meat jerky smoked at atmospheric pressure.

Dating back thousands of years, before the invention of refrigeration, freezing and canning processes, various meats and poultry were cured by natural smoke, and it has been found advantageous to smoke meats and poultry to preserve the foods and to impart a smoke flavor to enhance taste and acceptability. Meats and poultry have been smoked by the various smoking methods as described above.

However, one of the problems inherent in smoking meat products to impart preservation properties is that the smoke odor and/or smoke taste remains present in the meat flesh. Additionally, smoke that is produced from organic fuel materials typically contains particulates, such as creosote, tar, soot, etc., which are undesirable elements to have in contact with the meats. Thus, it is beneficial to provide a smoke that has had some of the particulate removed and further remove the smoke odor/taste while still maintaining the extended shelf life. Demand for smoked meats and poultry has been significant for many years and continues to grow.

In some cases, it is beneficial to use different woods to impart a specific flavour to the smoked proteinaceous food product. Various woods are used to impart different flavours. Woods that are commonly used for smoked foods include hardwoods, including the non-limiting examples of maple, mesquite, oak and hickory, which impart a medium to heavy flavour. Lighter woods, such as fruit- and nut-bearing woods, are used to impart a lighter flavour. Non-limiting examples of fruit- and nut-bearing woods include pecan, apple, pear, peach, cherry, and alder wood. Other plants can also be used to impart flavours to smoked foods, such as rosemary, thyme, sage, oregano, and other plants with essential oils that produce pleasant flavours.

One particular plant of interest that can be used in the smoking of proteinaceous foods is *Cannabis*, including pure varieties of *Cannabis*, or hybrid varieties produced by crossing *Cannabis sativa* and *Cannabis* indica. *Cannabis* is of interest for use in smoking foods because the plant contains cannabinoids, terpenoids, and other similar compounds that have known medical benefits for patients with a variety of ailments. Research has shown that *Cannabis* compounds can have beneficial health effects including reduction of pain, particularly neuropathic pain, treatment of chemotherapy-induced nausea and vomiting, and treatment of multiple sclerosis. It is also being researched for its use in preventing seizures and reducing inflammation. An increasing number of medical trials are being conducted to research other beneficial effects of *Cannabis* compounds in a wide variety of ailments. Current research includes work to examine the effects of *Cannabis* on cancer, dementia, diabetes, epilepsy, glaucoma, Tourette's syndrome, ALS, and various digestive diseases.

The use of *Cannabis* to treat symptoms has typically been achieved by smoking the plant or vapourizing it. The inhalation of *Cannabis* smoke results in a tar being deposited into the lungs that is chemically similar to that of tobacco smoke, with over 50 known carcinogens present. Accordingly, it is desirable to identify other means of delivering the beneficial compounds of *Cannabis* to the patient without the negative side-effects of smoking the drug.

Following the invention of refrigeration, the vitality of many such proteinaceous foods have been prolonged by maintaining these proteinaceous foods in chilled storage at temperatures of about 0° C. to about 6° C. Many such proteinaceous foods in their raw state begin rapid decomposition at temperatures above about 6° C. Hence, such proteinaceous foods can be maintained fresh and unfrozen for up to two to three weeks at temperatures of about 1° C. to about 6° C. However, both endogenous and microbial-induced decomposition is inevitable and rapid after this time period and other methods of freezing, canning, and smoking have been necessary to extend the shelf-life of these proteinaceous foods.

Since the advent of mechanical refrigeration, fish have been preserved by freezing and refrigeration, thus permitting fishermen to make longer fishing trips, as well as transport the fish long distances over land or water. It was determined that the vitality of whole or filleted fish have been prolonged by maintaining the fish in chilled storage at temperatures of about 0° C. to about 6° C. Fish, in particular in its raw state, begins decomposition quickly at temperatures above about 10° C. Fish can be maintained fresh and unfrozen for up to two to three weeks at temperatures of about 0° C. to about 4° C. However, decomposition is inevitable and rapid after this time period and other methods of freezing, canning, and smoking have been found necessary to extend the shelf life of the fish.

Most unfrozen fish is considered "fresh" for as many as about 21 days from harvest. However, unfrozen fish held at refrigeration temperatures for extended periods of time usually develop high levels of bacterial contamination which can lead to decomposition. Bacterial decomposition of fish includes the cellular breakdown of the flesh of the fish due to the hydrolytic enzymes of bacteria present on or within the flesh of the fish. Conversely, frozen fish is usually frozen upon harvest which reduces the likelihood that the fish will contain significant or harmful levels of bacterial decomposition.

The length of time over which fish maintains its freshness is commonly referred to as its shelf-life. The shelf-life of fish is determined by a number of factors, including the total number of each type of bacteria initially present, the specific types of bacteria present, the temperature of the flesh of the fish and of the surrounding atmosphere, and the pH of the fish. It is known that to extend the shelf life of fish, one may, for example, reduce the number of bacteria present using chemical means, freezing or other methods, create an acidic pH and/or maintain the product below about 5° C. in its fresh state. The most common process employed to extend the shelf life of fish is freezing.

An inherent problem, however, with freezing fish is its loss of the "fresh" attributes, e.g. a "pink" or "red" meat color to both the fish flesh and the "blood line" in the fish. The loss of these attributes causes the value of the frozen fish to be less than the value of fish that has not been previously frozen. This loss of value is an interpretation of the quality of the fish by the consumer. The color of the flesh and blood line of the fish is a major factor in the selling of seafood at the consumer level. Most consumers purchase fish with their "eyes" rather than with any other factor, such as smell, taste or texture. Therefore, it is desirable to maintain the "fresh" pink/red color of the seafood products as long as possible in order to sell the product at a premium to consumers.

Non-limiting examples of patents directed to the smoking of food products include the following:

U.S. Pat. No. 4,532,858, patented Aug. 6, 1985, by Hershfeld, provided apparatus for the surface application of liquid smoke to edible articles such as a link sausage product, cheese and other meat products. The patentee also taught that a shower of liquid smoke be re-circulated and that it may be heated to an elevated level. It was thus alleged that this method resulted in a faster and more efficient smoking process.

U.S. Pat. No. 5,368,872, patented Nov. 29, 1994, by Davis et al, provided a vacuum smoker for the smoking of foods. The smoke was first concentrated by the application of pressurized air. Then, that concentrated smoke was admitted into a vacuum smoking chamber under only a partial vacuum. Once the vacuum smoking chamber became filled with smoke-filled air, the vacuum smoke transfer means was disabled and the vacuum creation means further reduced the pressure within the vacuum smoking compartment still to an undefined partial vacuum. This process was frequently repeated so that new smoke frequently refilled the vacuum smoke compartment.

U.S. Pat. No. 5,484,619, patented Jan. 16, 1996 by Yamaoka et al, provided a procedure for smoking fish and meat by extra-low temperature smoking at extra-low temperatures, e.g., between about 0° C. and about 5° C.

U.S. Pat. No. 5,910,330, patented Jun. 8, 1999, by Fessman, provided a process for smoking foodstuffs located in a treatment chamber, using a mixture of superheated steam and liquid-form smoke vapor. The smoking with the mixture of superheated steam and liquid-form smoke vapor was carried out at a pressure of from about 2 to about 10 bars.

U.S. Pat. No. 5,972,402, patented Oct. 26, 1999, by Kowalski, provided a procedure for preparing seafood or meat by first treating the seafood or meat with purified smoke in plastic bags at temperatures between its freezing point and about 7° C. The so-treated seafood or meat was then frozen.

U.S. Pat. No. 6,777,012, patented Aug. 17, 2004, by Olson, provided a procedure for the preservation of meat products by a combination of smoke, ozone and freezing procedures.

U.S. Pat. No. 6,936,293, patented Aug. 30, 2005, by Yamaoka et al, provided a procedure for processing tuna meat by injection of smoke there into, and then freezing the resulting smoked tuna at −18° C.

AIMS OF THE INVENTION

Aims of the present invention include: to provide a method for smoke-infusing proteinaceous foods, e.g., cheeses, crustaceans, bivalve mollusks, gastropod mollusks, fish, meats and poultry, so that these particular smoke-infused proteinaceous foods, may be consumed locally or may be exported to distant export markets to result in maximized market value and economic return, since many of these distant export markets have high value perception; to provide a method for smoke-infusing such proteinaceous foods, which positively induces infusion or perfusion of the smoke into such proteinaceous foods; to provide a method for smoke-infusing proteinaceous foods, e.g., crustaceans, bivalve mollusks, gastropod mollusks, fish, meats and poultry and then quick freezing these particular smoke-infused proteinaceous foods, so formed so that these particular smoke-infused, proteinaceous foods, can be reconstituted by thawing for consumption of the thawed smoke-infused proteinaceous foods and when thawed may be cooked by usual means, e.g., of steam or hot water or microwave heating; to provide a method for smoke-infusing proteinaceous foods, e.g., crustaceans, bivalve mollusks, gastropod mollusks, fish, meats, cheeses and poultry with smoke that includes compounds derived from *Cannabis* plants in order to deposit onto said proteinaceous foods the medically active compounds in a consistent, measurable manner, such that a prescribed dosage of the compound can be consumed without the negative side-effects upon the lungs of inhaling the smoke of a cigarette made from *Cannabis* plant material; to provide a method for smoke-infusing proteinaceous foods, e.g., crustaceans, bivalve mollusks, gastropod mollusks, fish, meats and poultry thereby to prolong the vitality of these proteinaceous foods after these the above identified proteinaceous foods, e.g., crustaceans, bivalve mollusks, gastropod mollusks, fish, meats and poultry have been frozen and then thawed; to provide a method for smoke-infusing proteinaceous foods, e.g., crustaceans, bivalve mollusks, gastropod mollusks, fish, meats and poultry and then vacuum sealing these smoke-infused proteinaceous foods, so formed so that these smoke-infused proteinaceous foods so formed may be shipped as a frozen package to the ultimate user and then thawed and cooked by usual means, e.g., of steam or hot water or microwave heating, whereby, when thawed, these smoke-infused proteinaceous foods so formed would have characteristics of fresh smoke-infused proteinaceous foods i.e., taste attributes; to provide a method for smoke-infusing proteinaceous foods, e.g., cheeses, crustaceans, bivalve mollusks, gastropod mollusks, fish, meats and poultry in order to preserve the freshness, flavor, and shelf life of these smoke-infused proteinaceous foods so formed by inhibiting harmful bacteria and decomposition after such exposure to the ambient; to provide vacuum pack of smoke-infused proteinaceous foods, e.g., cheeses, crustaceans, bivalve mollusks, gastropod mollusks, fish, meats and poultry, preferably in a vacuum pouch, immediately after the smoke-infusing treatment, to protect the above identified smoke-infused proteinaceous foods so formed from contamination, and to seal in the smoke components which have been infused or perfused into the smoke-infused proteinaceous foods; and to provide a system for smoke-infusing proteinaceous foods, e.g., cheeses, crustaceans, especially cold-water clawed lobsters, bivalve mollusks, especially oysters, gastropod mollusks, especially abalones, fish, especially salmon and Arctic char, meat, especially beef brisket, and poultry, especially turkey and chicken which provides efficient infusion or perfusion of the smoke into these proteinaceous foods.

STATEMENTS OF INVENTION

One broad aspect of the present invention is the provision of a method of smoke-infusing proteinaceous foods, including inter alia, cheeses, e.g. cheddar cheese, crustaceans, e.g. cold water clawed lobsters, crabs, shrimps or crayfish, bivalve mollusks, e.g. oysters, clams or mussels, gastropod mollusks, e.g., abalones, fish, e.g., salmon, trout or Arctic char, meats, e.g. ham, sausage meat and sausages, pork, beef brisket, or reindeer, and poultry, e.g., chicken breast, turkey breast or duck breast, which comprises the steps of: enclosing the proteinaceous foods in a vacuum-treating zone; introducing smoke directly or indirectly from a smoke generation zone into the vacuum-treating zone; subjecting the proteinaceous foods to vacuum purging at a negative pressure in the vacuum-treating zone, thereby infusing smoke into such proteinaceous foods; repeating the steps of introducing smoke directly or indirectly from the smoke generation zone into the vacuum-treating zone, subjecting the proteinaceous foods to vacuum purging at a negative pressure in the vacuum-treating zone at least fifty times in pulsed sequences of smoke introduction stage/vacuum purging stage/vacuum release stage for the efficient infusion of smoke into such proteinaceous foods; a and post-chill resting cycle of the smoke-infused proteinaceous foods at a suitable temperature and for a suitable period of time. This provides proteinaceous foods in a form which have improved, acceptably-mild, smoky taste and which have enhanced preservation at ordinary refrigeration temperature.

Preferably this method includes the following further steps, namely introducing smoke directly or indirectly from a smoke generation zone into said vacuum-treating zone includes providing a smoke holding zone; recycling smoke from the smoke holding zone back into a conventional air inlet to the smoke generation zone; and introducing smoke from smoke holding zone into the vacuum-treating zone while the proteinaceous foods are subjected to vacuum purging at a negative pressure in the vacuum-treating zone. This method thereby increases the concentration of smoke in the smoke holding zone.

Preferably the negative pressure in the vacuum-treating zone is about 20 inches of Hg to about 29 inches of Hg, (which is traditionally defined as full vacuum), desirably from 22 inches of Hg to 29 inches of Hg and preferably from 26 inches of Hg to 29 inches of Hg (respectively, from about 515 mm Hg to about 735 mm Hg, desirably from about 565 mm of Hg to about 735 mm Hg and preferably from about 670 mm of Hg to about 735 mm Hg).

Preferably the repetitive cycle is up to about 400 or more pulsed sequences of smoke introduction stage/vacuum purging stage/vacuum release stage for the efficient infusion of smoke into the proteinaceous foods.

Preferably the pulsed sequences are carried out in a relatively short period of time, e.g. about 20 minutes to about 40 minutes.

Preferably the essential step of a chill resting cycle of such smoke-infused proteinaceous foods is at a temperature of between about 0° C. to about 6° C., preferably between about 2° C. and about 4° C., and is for a suitable period of time, i.e., for at least about 1 hour and preferably about 5 hours or more, e.g., between about 6 and about 10 hours.

The above-noted vacuum infusing steps by themselves have not been found to provide a delicate acceptably-mild smoky taste of the smoke-infused flavor to the proteinaceous foods.

What is essential is that, after the smoke infusing steps are carried out, the essential step of a chilled resting cycle must be carried out on the smoke-infused proteinaceous foods.

While not desired to be bound by theory, it is believed that the complex residue of smoke components on the proteinaceous food interacts with the smoke-infused proteinaceous foods and desirously adds to the flavor of smoke which is adhered to the proteinaceous food. It is further believed that the vacuum pulse process causes condensation of the smoke aerosol which is deposited onto the proteinaceous foods, as a liquid deposit of the complex molecules of the smoke, (e.g. tar, cresols, phenols, etc.). It is believed that the chilling of such smoke-infused proteinaceous foods for at least a five hour resting period cycle allows the complex molecules of the smoke to infuse and interact at the macromolecular level within the surface components of the particular proteinaceous foods.

While not desired to be bound by theory, it is also believed that infusion with trehalose takes advantage of the unique properties of trehalose sugar, which are known not to be found in other sugars to provide protection to hard shelled crustaceans, or soft shelled crustaceans or bivalve mollusks or gastropod mollusk under extended frozen storage. This permits re-constitution of such frozen hard shelled crustaceans or soft shelled crustaceans or bivalve mollusks or gastropod mollusks when they are thawed and cooked by usual means, e.g. by steam, hot water immersion cooking or microwave heating, with excellent taste and texture attributes. Trehalose has high water retention and protein preservation capabilities. Trehalose is thought to form a glass-phase as cells dehydrate which is believed to prevent disruption of internal cell organelles by effectively splinting them in position. It is believed that re-hydration then allows normal cellular activity to be resumed without major lethal damage that would normally follow a dehydration/rehydration cycle.

Another broad aspect of the present invention is the provision of such smoke-infused proteinaceous foods Another broad aspect of the present invention is the provision of such smoke-infused crustaceans and mollusks which are also infused with trehalose.

Another broad aspect of the present invention is the provision of such smoke-infused proteinaceous foods which are infused with smoke and which are provided in a vacuum pack.

Another broad aspect of the present invention is the provision of such smoke-infused crustaceans, bivalve mollusks, gastropod mollusks which are also infused with trehalose, and which are provided in a vacuum pack.

Another broad aspect of the present invention is the provision of such smoke-infused proteinaceous foods, including inter alia, cheeses, e.g. cheddar cheese, crustaceans, e.g. cold water clawed lobsters, crabs, shrimps or crayfish, bivalve mollusks, e.g. oysters, clams or mussels, gastropod mollusks, e.g., abalones, fish, e.g., salmon, trout or Arctic char, meats, e.g. ham, sausage meat and sausages, pork, beef brisket, or reindeer, and poultry, e.g., chicken breast, turkey breast or duck breast which are also infused with *Cannabis*-derived compounds which are deposited onto the surface of the food by the smoke that infuses said proteinaceous foods. These compounds may include cannabinoids, terpenes, terpenoids, flavonoids and other such compounds as are present in the *Cannabis* plant species.

Another broad aspect of the present invention is the provision of apparatus for smoke-infusing proteinaceous foods comprising: a source of smoke, e.g., a smoke generator; a smoke accumulation tank; a direct line connecting that source of smoke to the smoke accumulation tank; a first control valve operatively associated with the direct line connecting that source of smoke to the smoke accumulation tank; a recycle line from the smoke accumulation tank to an air inlet to that source of smoke, for the concentration of smoke in the smoke accumulation tank; a second control valve operatively associated with the recycle line connecting that source of smoke to the smoke accumulation tank; a vacuum-treating vessel, the vacuum-treating vessel being for holding the proteinaceous foods on support means; e.g., trays; a line connecting the smoke accumulation tank to the vacuum-treating vessel; a third control valve operatively associated with line connecting the smoke accumulation tank to the vacuum-treating vessel; a vacuum pump; a line connecting the vacuum pump to the vacuum-treating vessel for subjecting the vacuum-treating vessel to a negative pressure, for the efficient and active infusion of smoke into the proteinaceous foods; a fourth control valve operatively associated with the line connecting the vacuum pump to the vacuum-treating vessel; a fifth control valve operatively associated with the vacuum-treating vessel for the release of vacuum from the vacuum-treating vessel; and control means, either manual timing means or a programmable timing means controls for controlling the opening and closing of the first control valve, the second control valve, the third control valve, the fourth control valve and the fifth control valve for sequentially subjecting the vacuum-treating vessel to a plurality of pulsed sequences of smoke introduction/vacuum purging/vacuum release. This apparatus provides efficient infusion of smoke into the proteinaceous foods.

OTHER AIMS OF THE INVENTION

In carrying out preferred methods of the present invention, the following additional features, which may be claimed hereinafter include: selecting the negative pressure in the vacuum-treating zone preferably to be in the range of about 20 inches of Hg to about 29 inches of Hg, desirably from 22 inches of Hg to 29 inches of Hg and preferably from 26 inches of Hg to 29 inches of Hg (respectively, from about 515 mm Hg to about 735 mm Hg, desirably from about 565 mm of Hg to about 735 mm Hg and preferably from about 670 mm of Hg to about 735 mm Hg); selecting the smoke/air mixture to be either at atmospheric pressure or above atmospheric pressure; selecting the smoke/air mixture to have a moisture content of about 10% to about 50% by weight; selecting the smoke/air mixture to have a smoke content of up to about 50% by weight; selecting the at least fifty 50 pulsed smoke introduction/vacuum purging/vacuum release to comprise from about 50 to about 400 times; selecting those pulsed smoke cycles and the vacuum purging/vacuum release cycles to satisfy the following, namely, the smoke introduction takes place for about 1 second to about 10 seconds, the vacuum purging takes place for about 5 to about 30 seconds and the vacuum release takes place for about 1 second to about 10 seconds; selecting the post chilling cycle to be at a temperature of between about 0° C. to about 6° C., preferably between about 2° C. and about 4° C.; and selecting the time of the post chilling cycle to be at least about 1 hour and preferably 5 hours or more, e.g., between about 6 and about 10 hours.

One preferred embodiment involves carrying out the smoke infusing method which includes the application of vacuum, in the above-recited range with subsequent release of vacuum. It is believed that this vacuum permits substantially-instantaneous entry of the smoke enriched air-stream into the vacuum-treating zone and, thereby, effecting intimate contact between the smoke atmosphere and the hard and soft cheeses. While not desired to be bound by theory, it is believed that the absence of an air-surface barrier permits rapid and invasive perfusion of smoke volatiles and smoke solid particulates into the hard cheeses and soft cheeses, which is sufficient to impart a delicate smoke-infused flavor and odor to the hard and the soft cheeses.

This above-recited method for smoking cheeses improves the smoke flavor by conducting the vacuum-release smoke perfusion procedure in repeated cycles as desired to provide enhanced smoke flavor intensity. For optimized commercial production purposes, the vacuum pulse cycle can be repeated at least 50 times, i.e., between about 50 to about 400 cycles.

This above-recited method for smoking cheeses, also improves the overall flavor attributes of the rapid smoke-infusing procedure by a post-smoke resting cycle at chill room temperatures of, e.g. about 1° C. to about 6° C. for a suitable period of at least 1 hour and preferably 5 hours or more, e.g., between about 6 and about 10 hours. This procedure enables harsh volatile smoke components partially to volatilize, thereby conferring a smoothness of flavor to the finished smoked cheeses.

In another preferred embodiment when the hard shelled crustaceans, e.g., cold-water clawed lobsters and crabs, are smoked according to embodiments of this invention, the integrity of the delicate smoke-infused-flavored myotomal tissue of these hard shelled crustaceans is maintained under storage. The so-infused hard shelled crustaceans may then be thawed and cooked by usual means, e.g., by steam cooking by or hot water immersion or microwave heat cooking. The resultant such hard shelled crustaceans have been found to acquire a delicate cold-smoke-infused flavor and to retain taste and other desirable qualities after reconstitution which are sufficient to yield a high quality edible such hard shelled crustaceans.

In another preferred embodiment of the present invention, where the particular crustaceans proteinaceous foods, are, e.g. cold-water clawed lobsters, crabs, or shrimp, the following are further steps carried out on such crustaceans, whether taken singly or in combination: and which may be claimed hereinafter: subjecting the so-treated smoke-infused crustaceans to conventional freezing techniques; subjecting such crustaceans, prior to the smoke-infusing procedure, to a hot water immersion, e.g. at about 55° C. to about 65° C. for a suitable period of time, e.g. a time about 1 to about 8 minutes, which is sufficient to kill the crustaceans humanely, and then optionally subsequent rapid chilling, e.g. through exposure to ice-water for a suitable period of time, e.g. up to about 30 minutes; exposing such crustaceans to conditions of high externally-applied pressure, preferably about 20,000 psi to about 40,000 psi (about 140,000 kPa to about 280,000 kPa) for a suitable period of time, preferably about 2 to about 20 minutes which is sufficient to kill the live crustaceans humanely, while substantially and simultaneously tenderizing the raw myotomal tissue thereof; subjecting cold-water clawed lobsters or crabs, prior to the smoke-infusing procedure, to at least one of the following steps, namely: a) the step of removal of the visceral content of the cold-water clawed lobsters or crabs, e.g. by a vacuum procedure, or by positive pressure water flushing and expulsion of the gastro-intestinal content, preferably by effecting a bilateral incision along the ventral surface of the cold-water clawed lobsters or crabs, and application of bi-directional external pressure applied to the thoracic carapace region and sufficient to permit gastro-intestinal tract removal and flush cleaning, e.g. by flushing with a solution of trehalose sugar, preferably at a concentration of about 1 to about 5% by weight within the cleansed cavity and gaped ventral tail myotomal tissue, e.g. by means of high pressure spray irrigation; subjecting the cold-water clawed lobsters or crabs, prior to the smoke-infusing procedure, to at least one of the following steps: b) exposing the hard shelled crustaceans to a hot water immersion at a suitable temperature of about 55° C. to about 65° C., for a suitable period of time which is sufficient to kill such cold-water clawed lobsters or crabs, humanely, and subsequently rapid chilling of the cold-water clawed lobsters or crabs, e.g. through exposure to ice-water for a suitable period of time, e.g., at least about 3 minutes, preferably about 3 to about 6 minutes; c) immersing the so-treated cold-water clawed lobsters or crabs, into a chilled salt solution, e.g. of a concentration of about 1% to about 5% by weight at a suitable temperature of e.g. about 0° C. to about 4° C.; subjecting the cold-water clawed lobsters or crabs, either prior to the smoke-infusing procedure, or after the smoke-infusing procedure, to at least one of the above-recited steps and then of following steps: d) treating the cold-water clawed lobsters or crabs, with a trehalose solution of a suitable concentration of, e.g. about 1% to about 5% by weight for a suitable period of time; e) immersing the so-treated cold-water clawed lobsters or crabs, into a chilled salt solution at a temperature of about 0° C. to about 4° C., the salt solution being of a concentration of about 1% to about 5% by weight and then treating the so-treated cold-water clawed lobsters or crabs, with a trehalose solution which is of a concentration of e.g. about 1% to about 5% by weight for a suitable period of time which is about 1 minute to about 5 minutes, and then draining for a suitable period of time, preferably about 1 minute to about 3 minutes, and then preferably subjecting the so-treated cold-water clawed lobsters or crabs, to a conventional freezing technique; incision of the integuments joining the external hard shell components of the cold-water clawed lobsters or crabs, such components preferably being the leg joint, the front claw and the ventral surface tail carapace; f) draining such cold-water clawed lobsters or crabs, for a suitable period of time, e.g. between about 1 to about 3 minutes and subjecting them to standard industry procedures of brine freeze immersion or, if not yet smoke-infused, directing them to the smoke-infusing procedure.

The smoke-infusing method of aspects of the invention has been found to extend the shelf life of substantially all crustaceans and permits such crustaceans to maintain their freshness and freedom from bacterial decomposition for long periods of time following catch. The smoke preservation method further maintains characteristics of such crustaceans, such as, taste, texture and color, thus making the frozen and then thawed re-freshed crustaceans produced by the present method more appealing to consumers.

While the method described herein, also involves the treatment of fresh fish, a similar process can be applied to frozen fish. One such method is to thaw the frozen fish and later apply the smoke to the thawed fish. A preferred method of treating frozen fish is simultaneously to thaw and smoke the fish in the smoking apparatus. This eliminates the exposure of the fish to standard atmosphere as it thaws.

In another preferred embodiment, the technique of immersing live bivalve mollusks, e.g. oyster, clams, mussels in a solution of salt-water containing trehalose solution in the amount of between 1% to 5% by weight for a period of between 0.5 to 2 hours has been shown to confer on said live bivalve mollusks an enhanced robustness of myotomal tissue in subsequent processing involving the use of rapid freezing methods and prior exposure to smoke infusion techniques as described herein. The protective capacity of trehalose sugar applied to the delicate muscle tissue of live bivalve mollusks assists in maintaining the integrity of said tissue under subsequent processing and later reconstitution by cooking methods. In particular, the trehalose immersion procedure enhances the shelf-life and survivability of the live bivalve mollusks, e g, oyster, clams and mussels during exposure to repeating cycles of vacuum pulsed smoke infusion.

In another preferred embodiment of the present invention, the proteinaceous foods are poultry, e.g. chicken, turkey, duck, ostrich or emu; and meats, e.g., beef, pork, sheep, veal, reindeer or goat. While the method described herein involves the treatment of fresh poultry or meats, a similar process can be applied to frozen poultry or meats to smoke-infuse them. One such process is to thaw the frozen poultry or meats and later apply the smoke to the thawed poultry or meats. A preferred method of treating frozen poultry or frozen meats may be simultaneously to thaw and to smoke the frozen poultry or frozen meats in the smoking apparatus. This eliminates the exposure of the poultry or meats to the ambient atmosphere as they thaw.

The vacuum smoke-infusing preservation method of aspects of the invention has been found to be effective in prolonging the vitality of poultry or meats. The vitality-preserving effects of the vacuum smoke-infusing preservation method survive freezing and thawing, as well extending the shelf-life of the smoke-infused poultry or meats and maintaining its freshness and freedom from bacterial decomposition for long periods of time The vacuum smoke-infusing preservation method of aspects of the invention further maintains the characteristics of smoke-infused poultry or meats, such as taste, texture and color, making the thawed and later re-constituted smoke-infused poultry or meats produced by the present method more appealing to consumers.

GENERALIZED DESCRIPTION OF THE INVENTION

As used herein, the term "proteinaceous foods" is intended to include, inter alia cheeses, hard shelled crustaceans, e.g., lobsters or crabs, soft shelled crustaceans, e.g., shrimps or crayfish, mollusks, e.g., oysters, clams, or mussels, fish, e.g., salmon, trout or Arctic char, meats and fowl, e.g., ham, bacon, beef jerky, sausage, chicken breast and turkey breast, beef brisket, reindeer, chicken, turkey, duck, etc. Such smoked proteinaceous food products are all some non-limiting examples of popular foods which have been treated by smoke. Thus, the term "proteinaceous food" is intended to mean the following.

Cheese. By the term "cheese" is meant both hard and soft cheeses Examples of cheeses include: American cheeses including, but not necessarily limited to American Asiago, American Brick, American Cheddar, American Colby, American Colby-Jack, American Farmers, American Monterey Jack, American Marble Cheddar, American Mascarpone, American Muenster, American Pepper Jack and American Swiss; Austrian cheeses including, but not necessarily limited to Austrian Gruyere, Austrian Fontina, and Lunenburg; Belgium cheeses including, but not necessarily limited to Belgian Cheddar, Bruges Gold, and Brussels, British cheeses including, but not necessarily limited to, Caerphilly, Cheddar, Cheshire, Derby, Double Gloucester, Lancashire, Red Lancashire, Red Windsor and Stilton Cheddar; Canadian cheeses including, but not necessarily limited to, Canadian Brick, Canadian Cheddar, Canadian Farmers, Canadian Havarti, Canadian Marble Cheddar, Canadian Monterey Jack, Canadian Mozzarella, Canadian Parmesan, Canadian Racklette, Canadian Swiss and Oka; Danish cheeses including, but not necessarily limited to Danbo, Esrom, Danish Havarti, Danish Tilsit-Havarti, and Somsoe; Dutch cheeses including, but not necessarily limited to Edam, and Gouda; French cheeses including, but not necessarily limited to Beaufort, Camembert, Epoisses, French Emmenthal, French Munster, French Rackette, and Port Salut; Finnish cheeses including, but not necessarily limited to Lappi and Finlandia; German cheeses including, but not necessarily limited to Allgau, Bierkasse, German Emmenthal, and German Tilsit; Italian cheeses including, but not necessarily limited to Asiago, Bel Paese, Bocconcini, Fontina, Gorgonzola, Mozzarella, Parmesan, Provolone, Ricotta and Romano; Irish cheeses including, but not necessarily limited to Coolea, Corleggy and Dubliner; Norwegian cheeses including, but not necessarily limited to Gamalost, Geitost, Jarlsberg and Norvegia; Swedish cheeses including, but not necessarily limited to Swedish Farmers and Swedish Fontina; Swiss cheeses including, but not necessarily limited to Emmenthal, Fribourgeouse, Gruyere, Neufchatel, and Vacherin. Preferred cheeses include, but are not necessarily limited to, cheddar, gouda, mozzarella and gruyere.

Crustaceans. The term "crustaceans" includes, a) Lobsters including, but not necessarily limited to Cold Water Clawed Lobsters including, but not necessarily limited to American Cold Water Clawed Lobsters and Canadian Cold Water Clawed Lobsters, Bight Lobsters, Brazilian Lobsters, and European Lobsters; b) Crayfish, including, but not necessarily limited to Caribbean Lobsters, Crawdads, Dublin Prawns, European Crayfish, Japanese Lobsters, Langoustines, New Zealand Lobsters, Norwegian Lobsters, Scampi, Sea Crawfish and Spiny Lobsters; c) Crabs, including, but not necessarily limited to Blue Crabs, Common Crabs, Dungeness Crabs, European Spiny Crabs, Flower Crabs, Golden Crabs, Japanese Blue Crabs, Jonah Crabs, King Crabs, Peekytoe Crabs, Porcupine Crabs, Red King Crabs, Snow Crabs, Southern Rock Crabs, Stone Crabs including Northern Stone Crabs and Florida Stone Crabs and Toad Crab; d) Prawns, including, but not necessarily limited to Common Prawns, Tiger Prawns including Black Tiger Prawns and Giant Tiger prawns and Indian Prawns; and e) Shrimp, including, but not necessarily limited to American Freshwater Shrimp, Amino Shrimp, Giant Shrimp, Jumbo Shrimp, Tiger Shrimp including Black Tiger Shrimp, Penaeid Shrimp including White Shrimp, Pink Shrimp and Brown Shrimp, Sand Shrimp, Sri Lanka Dwarf Shrimp, Thai Shrimp and Yellow Nose Shrimp.

Bivalve Mollusks, Gastropods and Cephalids, namely a) Bivalve mollusks, including, but not necessarily limited to clams including, but not necessarily limited to Atlantic Surf Clams, Pacific Razor Clams, Quahogs, Razor Clams, Surf Clams, and Soft Shell Clams (steamers), Cockles, Mussels, Oysters and Scallops; b) Gastropods including, but not necessarily limited to Abalones including, but not necessarily limited to Northern Pinto Abalones, Ormers, Muttonshells, Conch, Snails including, but not necessarily limited to Fresh Water Snails, Land Snails and Limpets and Sea Snails, and Whelks; and c) Cephalids, including, but not necessarily limited to Cuttlefish and Octopus and Squids, including, but not necessarily limited to Argentinean Short Fin Squids, Longfin Squids, Japanese Flying Squids and Patagonian Squids.

Fish. The term 'fish' includes both "freshwater fish" and "marine fish" and includes, fish per se and also the roe of such fish, but is not limited to Arctic char, bass, blowfish, bluefish, bonito, brill, carp, capelin, catfish, chub, cobia, cod, conger, dolphin, dore, eel, European anchovy, Flying fish, flounder, fluke, gar, grayling, grouper, hake, halibut, haddock, herring, jack, John Dory, king fish, lamprey, lake trout, loach, mackerel, mahi-mahi, marlin, moray eel, mullet, orange roughy, perch, pike, pike-perch, pilchard, plaice, Pollock, pompano, porgies, rainbow trout, salmon and salmon roe, including but not limited to Atlantic salmon, Coho salmon, Chinook salmon and salmon-trout, sardine, scrod, sea bass, sea bream, sea squab, seat trout, shad, smelt, snapper, sole, spade fish, sprat, sturgeon including its caviar, sword fish, tarpon, tilapia, tile fish, turbot, trevally, tunas including albacore tuna, big eye tuna, blue fin tuna, tongol tuna, skipjack tuna and yellow fin tuna, Wahoo, walleye, white croaker, white grunt, whiting, whitefish, and Winnipeg Goldeye.

Meats and Poultry which includes the edible meat from the genus *Bos* (e.g. cows), the genus *Os* (e.g. pigs), the genus *Ovis aires* (e.g. sheep), the genus *Capra*(e.g. goat), the genus *Rangifer tarandus* (e.g. reindeer), the genus *Cervus elaphus* (e.g., elk), the genus *Alces alces* (e.g., moose), the genus *Damalisus* sub-family Antilopinae (e.g. antelope), and which also includes edible meat from the genus *Galloanserae* (e.g., fowl), especially of the order Galliformes (e.g. chickens, quails and turkeys) and the genus *Anatidae* in the order Anseriformes (e.g., domestic ducks and domestic geese), etc. Specifically for a) beef, the butcher cuts of which include, but are not limited to brisket, brisket point porterhouse, prime rib, rib eye, round, short loin, sirloin hip, sirloin tip, tenderloin, top sirloin and T-bone and ground or minced beef; Specifically for b) veal, the butcher cuts of which include, but are not limited to breast, butt, flank, leg, loin, rump, sirloin and sirloin tip and ground or minced veal; Specifically for c) pork, the butcher cuts of which include, but are not limited to belly, breast, chops, ham, loin, picnic, shoulder and tenderloin and ground or minced pork or minced or ground pork sausage meat, which includes other ingredients including cereal, spices etc.; Specifically for d) sheep and lamb, the butcher cuts of which include, but are not limited to double shoulder, flank, leg, leg shank, loin and sirloin and ground or minced sheep or lamb; Specifically for e) deer, including reindeer, antelope, elk and moose, the butcher cuts of which include, but are not limited to back rib, brisket, chuck, hip, flank, loin, loin strips, roast, saddle, short loin, steak, tenderloin and top sirloin, and ground or minced deer; f) goat, the butcher cuts of which include, but are not limited to leg, rack, short loin, tenderloin and ground or minced goat.

Poultry, including but not limited to chicken, emu, turkey, duck, goose, ostrich, squab, and quail, the butcher cuts of which include, but are not limited to back, breast, breast strips, cutlets, drumsticks, legs, tenderloins thighs and wings.

Common examples of these meats and poultry that may be smoke-infused include sausage ground pork and sausages, bacon, ham, brisket, pastrami, salami, reindeer, reindeer steak, and reindeer fillet, and turkey breast, turkey thighs, turkey legs, chicken breast, chicken thighs, chicken legs, duck breast, duck thighs duck legs, ostrich breast, ostrich thighs, ostrich legs, and the like.

DETAILED DESCRIPTION OF THE DRAWINGS

Figure 1:
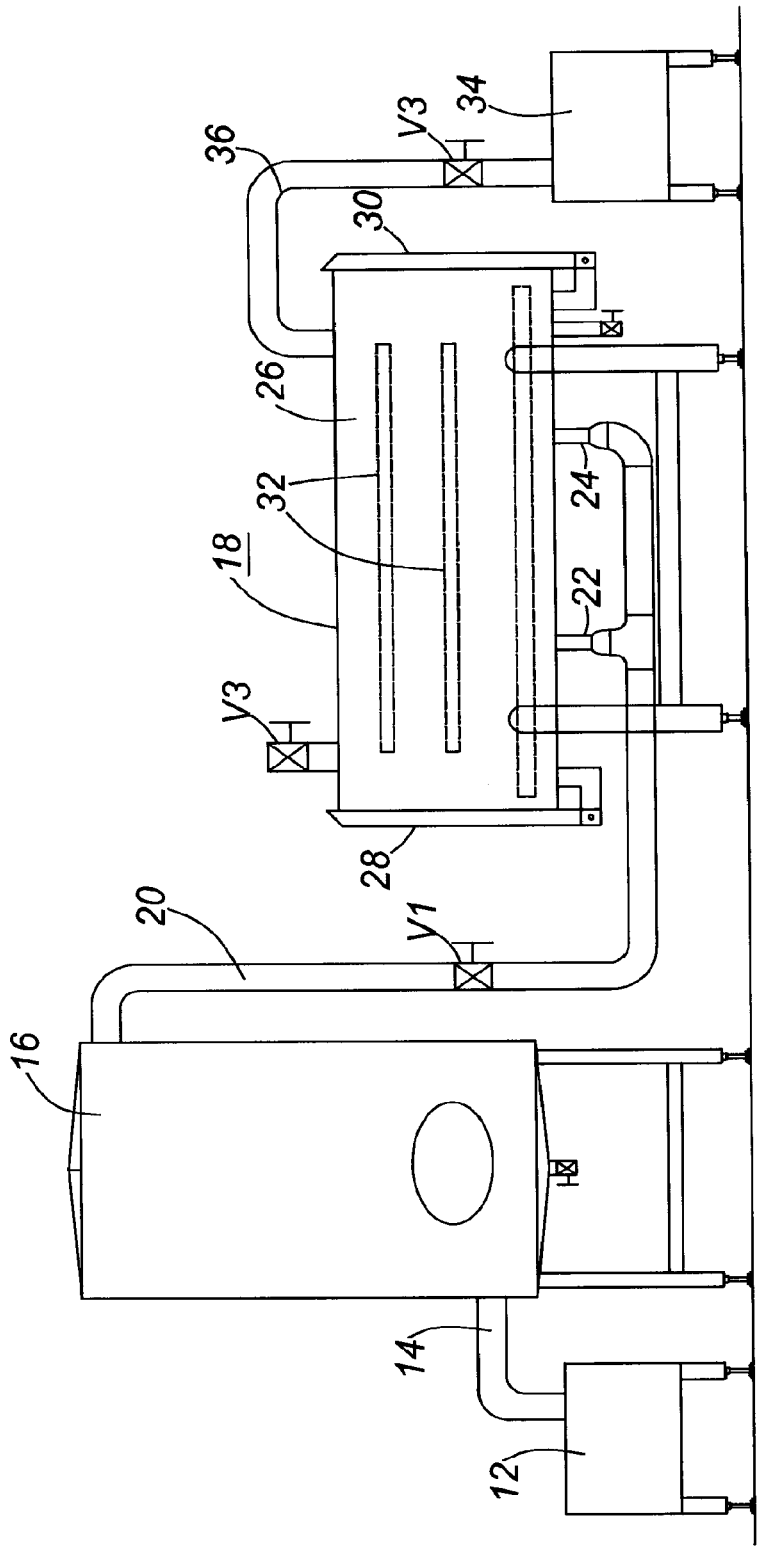
FIG. 1 is a schematic, generalized side-elevation view of a vacuum smoke-infusing apparatus which may be employed for carrying out the method of a broad aspect of the present invention.
Figure 2:
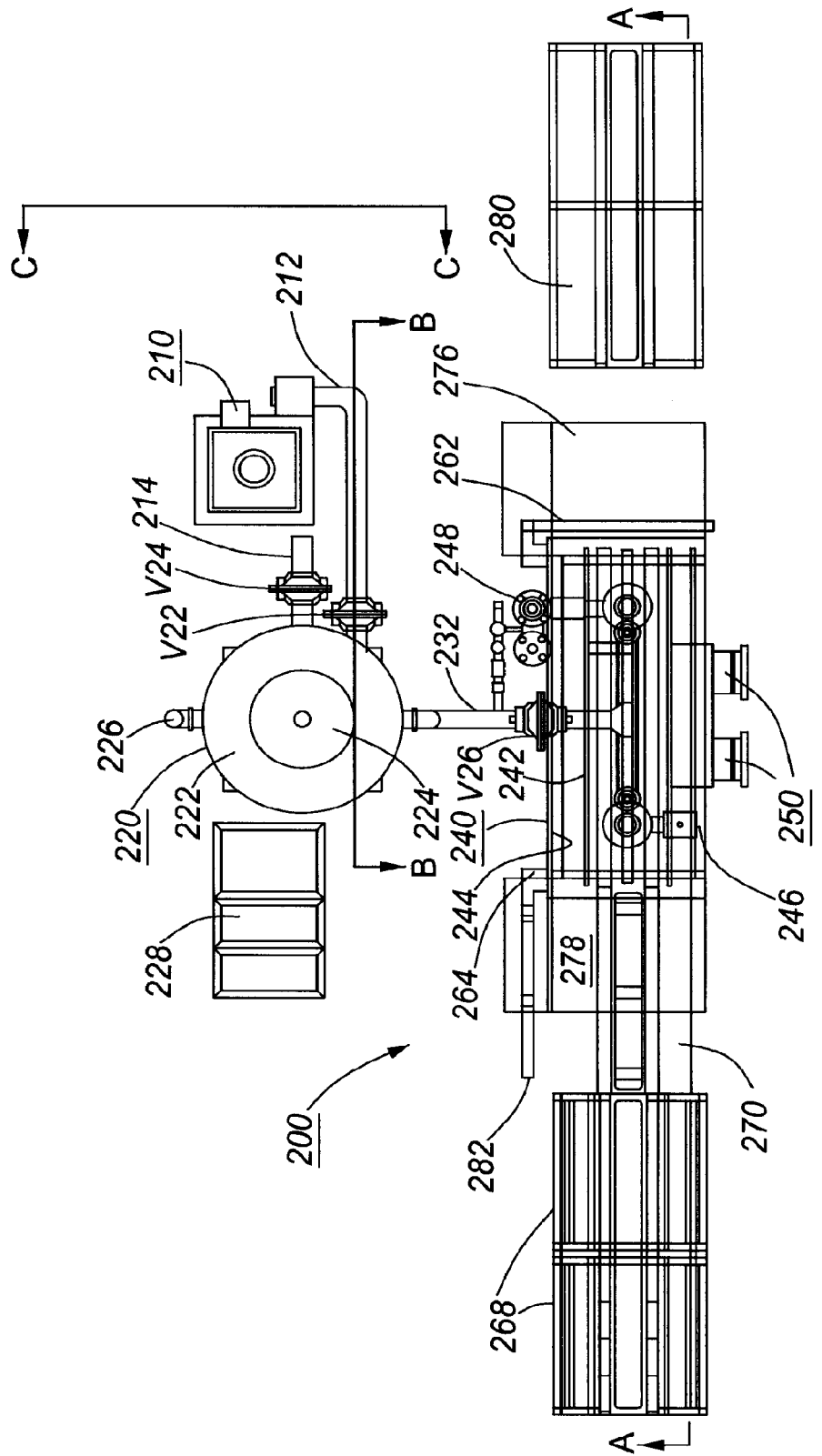
FIG. 2 is a top plan view of a prototype of a commercial vacuum smoke-infusing apparatus which has been employed for carrying out the methods of the present invention as described in the following examples.
Figure 3:
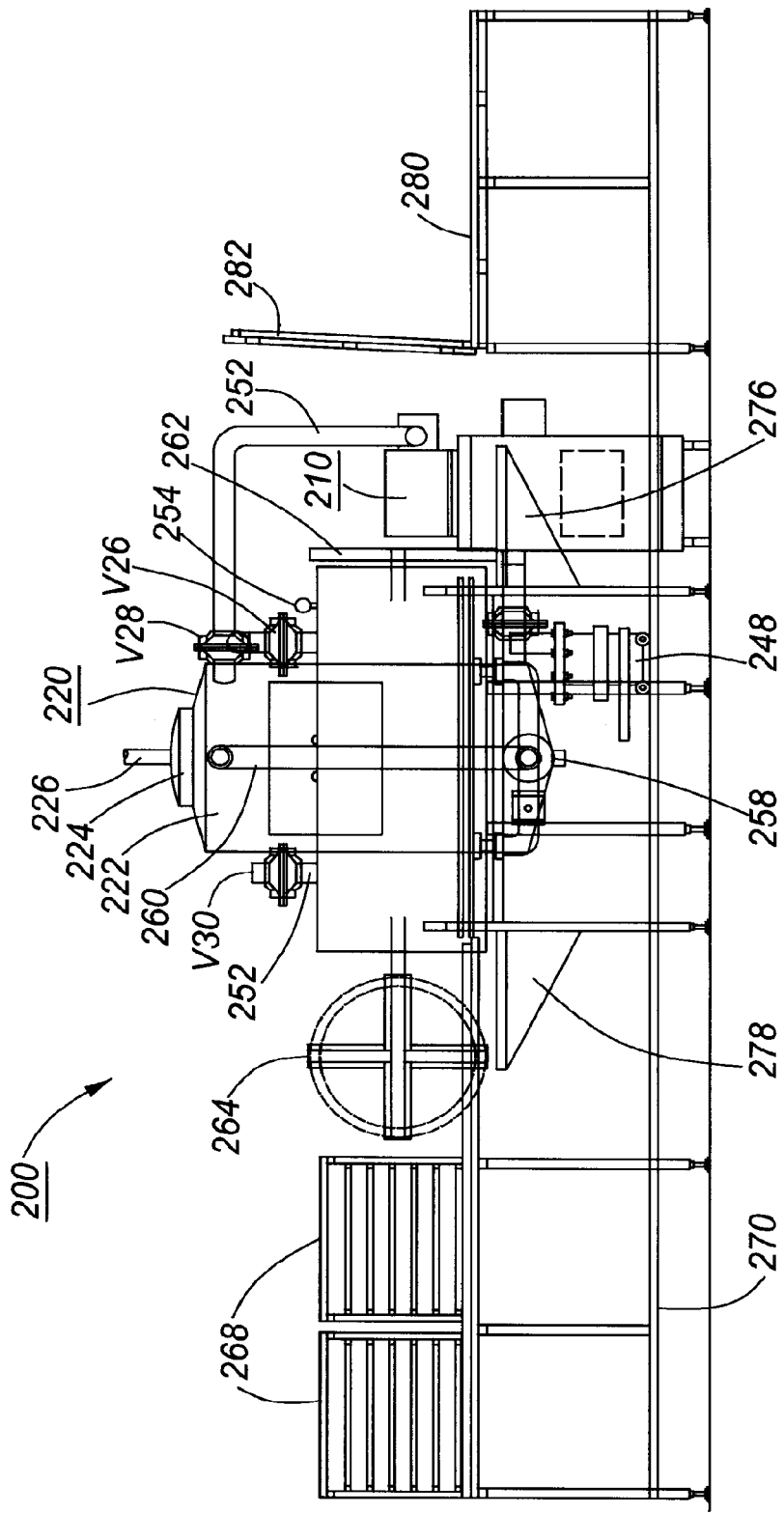
FIG. 3 is a side-elevation view of the prototype commercial vacuum smoke-infusing apparatus shown in FIG. 2, taken along the arrows A-A.
Figure 4:
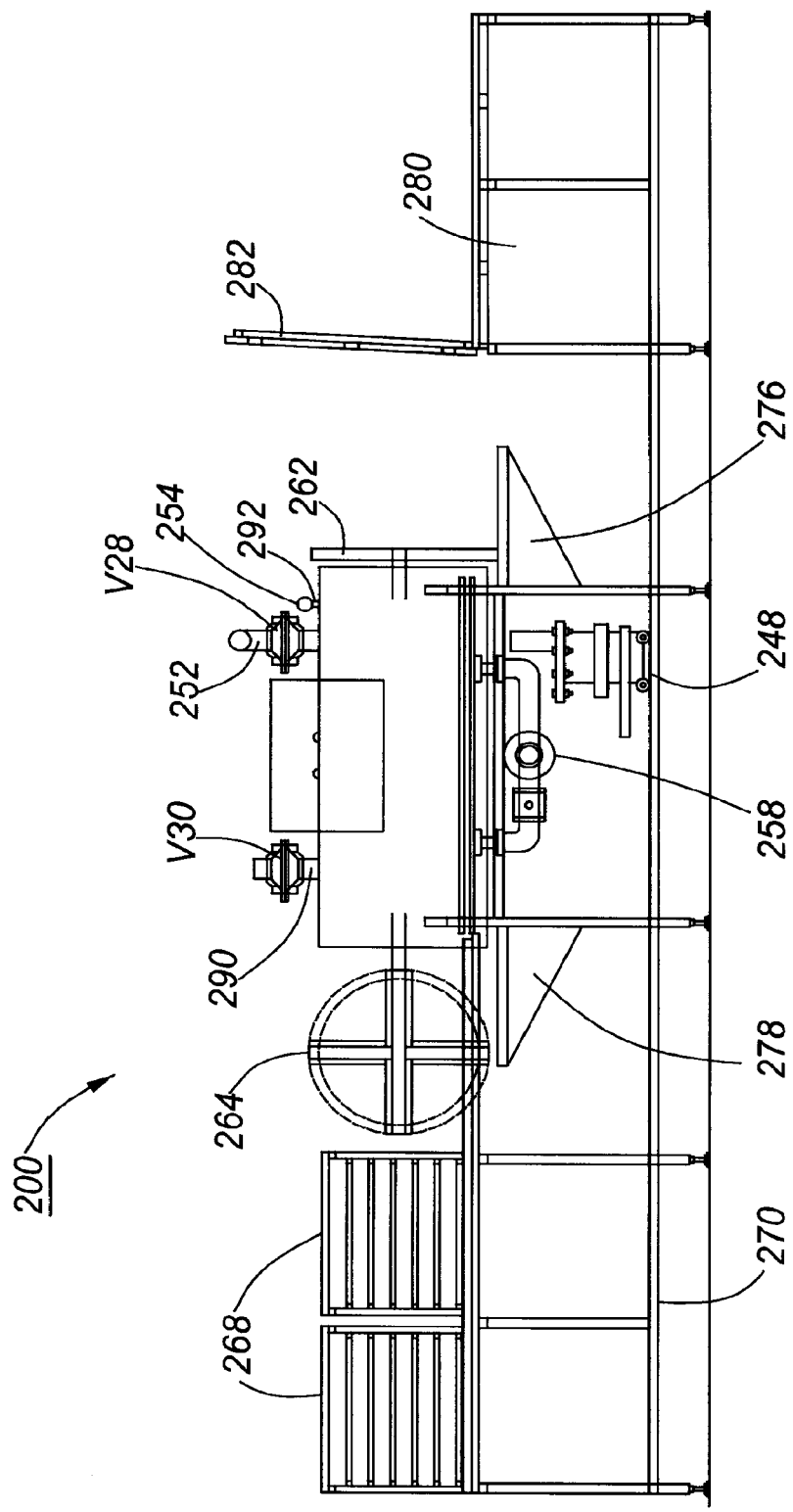
FIG. 4 is a side-elevation view of the prototype commercial vacuum smoke-infusing apparatus shown in FIG. 2, taken along the arrows B-B.
Figure 5:
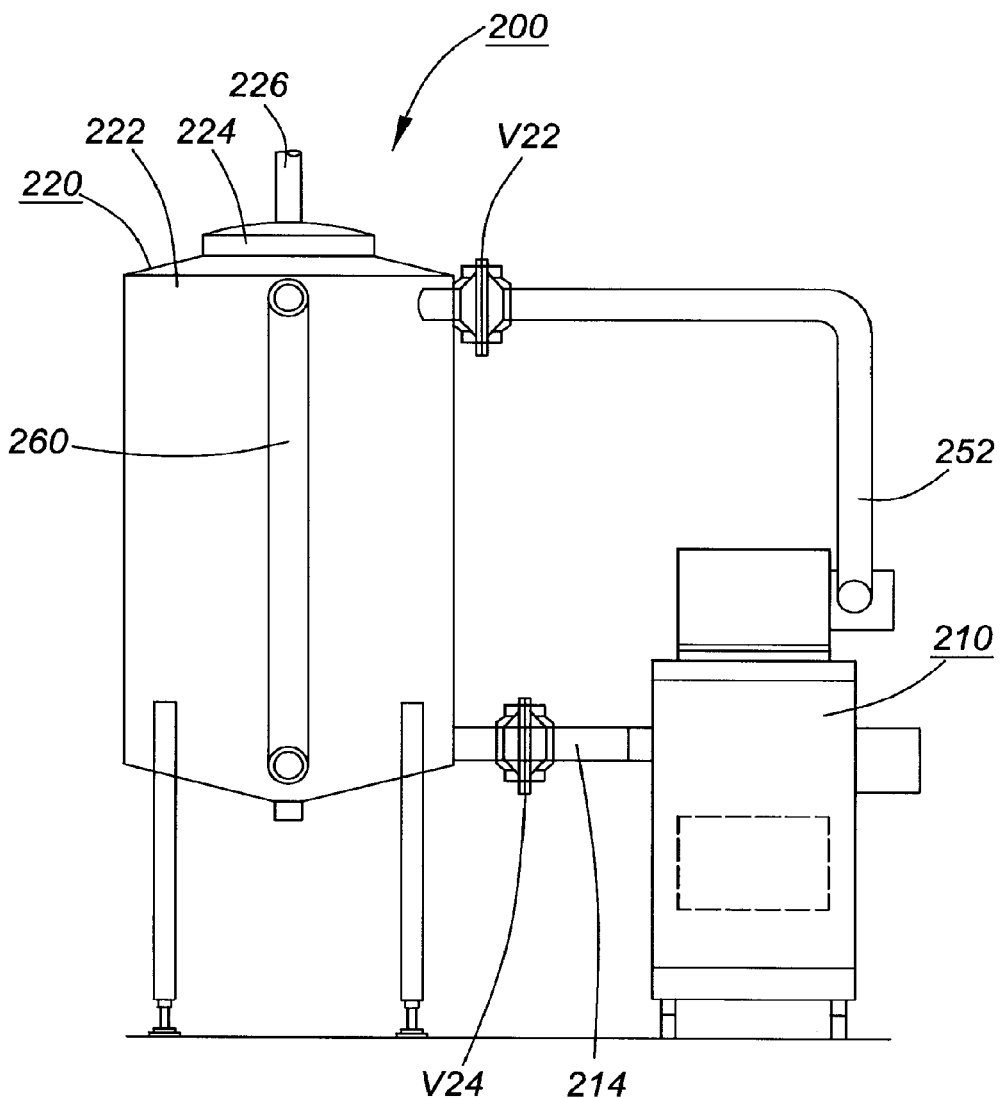
FIG. 5 is an end elevation view of the prototype commercial vacuum smoke-infusing apparatus shown in FIG. 2, taken along the arrows C-C.

Detailed Description of FIG. 1

The vacuum smoke-infusing apparatus 10 comprises a smoke generator 12 connected by piping 14 to an accumulation tank 16. The accumulation tank is connected to a vacuum-treating vessel 18 by means of line 20 which is provided with a first control valve V1. Line 20 leads via branches 22, 24 to the interior 26 of the vacuum-treating vessel 18. The vacuum-treating vessel 18 includes two vacuum sealed tight closure doors 28, 30. Within the interior 26 of the vacuum-treating vessel 18 are a plurality of trays 32 or other means, for holding the proteinaceous foods to be smoke-infused. The vacuum-treating vessel 18 is placed under sub-atmospheric pressure within the range of about in the range of about 20 inches of Hg to about 29 inches of Hg, desirably from 22 inches of Hg to 29 inches of Hg and preferably from 26 inches of Hg to 29 inches of Hg (respectively, from about 515 mm Hg to about 735 mm Hg, desirably from about 565 mm of Hg to about 735 mm Hg and preferably from about 670 mm of Hg to about 735 mm Hg) by means of vacuum pump 34, which is connected to vacuum-treating vessel 18 by line 36 which is fitted with a second control valve V2. Vacuum-treating vessel 18 is also fitted with a third valve control V3. While not shown, the vacuum-treating vessel 18 is preferably provided with vacuum gauge to provide information on the vacuum within the vacuum-treating vessel 18.

Control Valves V1, V2 and V3 are controlled either manually or by programmable controls to subject the proteinaceous foods to vacuum perfusion at the above recited negative pressure in the vacuum-treating zone. This perfusion is carried out at least about 50, and up to about 400 or more, times in pulsed sequences of smoke introduction stage/vacuum purging stage/vacuum release stage for the infusion of smoke into proteinaceous foods. These cycles of repeated sequences are carried out in such pulsed sequences in a relatively short period of time, e.g. about 20 minutes to about 40 minutes for the efficient infusion of smoke into the proteinaceous foods. As noted above, the control of control valves V1, V2 and V3 may be by manual timing means or but are preferably automatically controlled by suitable controls, e.g. an Allen Bradley Micrologic 1000™ Programmable Controller.

The smoke generator 12 produces smoke suitable for treatment of the previously recited proteinaceous foods for human consumption and has a smoke/air mixture moisture content of about 10% to about 50% by weight. This smoke/air mixture may be generated by any number of means including, but not limited to, combustion, transformation between solid or liquid state to gaseous state, friction, pyrolysis, aerobically, anaerobically, electrical heating or direct flame; and the smoke may be used in its whole or filtered state. If the smoke is filtered to remove any component of the smoke, such filtering may be performed by any physical means, carbon filtering, ice column filtering, centrifugal force, electrostatic force, or other known means of separating out a component of smoke. The burning of wood sawdust, in an oxygen restricted retort, is an efficient way to produce high quality smoke from woods. Typical wood fuels for smoking include oak, spruce Japanese oak, beech, cherry, alder, Japanese linden, walnut, chestnut, white birch, hickory, poplar and plane, chinquapin, Japanese common chestnut, and other trees. Typical non-wood fuels for smoking include dried peat.

The smoke generator 12 may be any commercially-available smoker apparatus, e.g., that which may be obtained commercially from Scott Engineering, Indianapolis, Ind., USA, or from KOCH Equipment L.L.C. Kansas City, Mo., U.S.A., or from AFOS Group, Hesle, England.

Detailed Description of FIG. 2, FIG. 3, FIG. 4 and FIG. 5

The vacuum smoke-infusing apparatus 200 of a broad aspect of the present invention includes three main units, namely a smoke generator 210, a smoke accumulation tank 220 and a vacuum-treating vessel 240, which are all interconnected.

The smoke generator 210 is connected to the accumulation tank 220 by means of recycle line 212, which may be, for example, a 3" sanitary tube with ferrules and clamps, for recirculation of air between the air inlet (not seen) of smoke generator 210 and the accumulation tank 220. In order to assist in the recycling of the smoke from the smoke generator 210 to the accumulation tank 220, a blower, (not seen) is connected to a conventional air inlet to the smoke generator 210 A suitable control valve V22, which may be, for example, a 3" pneumatically-operated butterfly valve, is provided in recycle line 212. Control valve V22 is controlled to be a re-circulated air/smoke mixture shut-off valve.

The smoke generator 210 is also connected to the accumulation tank 220 by means of direct line 214, which may be, for example, a 3" sanitary tube with ferrules and clamps, for direct introduction of smoke from smoke generator 210 to the accumulation tank 220. A suitable control V24, which may be, for example, a 3" pneumatically-operated butterfly valve, is controlled to be an air/smoke mixture shut-off valve.

The smoke accumulation tank 220 is a generally-cylindrical upright hollow cylinder 222 which is provided with a man-way 224 which leads to a vent 226. Access to the interior of the accumulation tank 220, for any reason, is achieved through man-way 224 via access steps 228.

The smoke generator 210 produces a smoke/air mixture which is suitable for treatment of the previously recited proteinaceous food products. The smoke generator 210 includes an air inlet (not seen) to enable the production of smoke. The smoke generator 210 produces smoke which preferably has a smoke/air mixture moisture content of about 10% to about 50% by weight. The recycling units described above ensure that the smoke, in the smoke/air mixture, may be up to about 50% by weight. This smoke/air mixture may be generated by any number of means, using the above-recited commercially-available smokers, including, but not limited to, combustion, transformation between solid or liquid state to gaseous state, friction, pyrolysis, aerobically, anaerobically, electrical heating or direct flame; and the smoke may be used in its whole or filtered state.

If the smoke in the smoke/air mixture is filtered to remove any component of the smoke, such filtering may be performed by any physical means, e.g., carbon filtering, ice column filtering, centrifugal force, electrostatic force, or other known means of separating out a component of smoke. The burning of wood sawdust, in an oxygen restricted retort, is an efficient way to produce high quality smoke from woods. Typical wood fuels for smoking include oak, spruce Japanese oak, beech, cherry, alder, Japanese linden, walnut, chestnut, white birch, hickory, poplar and plane, chinquapin, Japanese common chestnut, and other trees. Typical non-wood fuels for smoking include dried peat and coconut fibre.

Wood sawdust can be compressed into a pelletized format that makes it more convenient to burn and extends the burning time in comparison to loose sawdust. Prior to pelletizing, other components can be added to the sawdust in measured amounts and thoroughly mixed with the sawdust prior to being compressed into pellets. In particular, a measured amount of *Cannabis* plant material can be added to the sawdust and thoroughly mixed with the sawdust prior to pelleting. This will result in a pellet containing a measurable percentage of *Cannabis* plant material allowing for a measured dose of *Cannabis* compounds to be deposited on the proteinaceous food being smoked. This is preferable to burning the *Cannabis* plant in a loose or dried format because it will burn very quickly and produce less smoke. The aims of the invention could be achieved by using wood chips mixed with *Cannabis* material, or by burning the material by itself, but these methods are not as efficient as the pelletized fuel, which results in a precision smoking technique that is repeatable and measurable. By adding the *Cannabis* material to the sawdust and forming pellets, a more efficient burning process will occur during which the *Cannabis* material will slowly burn and release its compounds. The *Cannabis* plant is not used without being mixed with some material derived from an appropriate wood or non-wood fuel as described above. By itself, the *Cannabis* plant produces excessive amounts of material that deposit onto the smoked food and produce an unpleasantly harsh flavour.

The smoke generated from burning the *Cannabis* plant material produces a sticky residue containing a complex of *Cannabis* compounds, which is deposited on the surface of the food being smoked during the smoking process as described herein. This deposit is thickest when the bud portion of the *Cannabis* plant is used because the bud material contains the highest concentration of the active compounds. When a mixture of stem and leaf material is used in the smoking process, the amount of deposited residue is lower than when the bud portion is used. The material commonly referred to as "shake" contains a mixture of *Cannabis* bud, leaf and stem material. This can also be used for the smoking process described herein, and will result in a moderate amount of the *Cannabis* compound complex being deposited on the food, although the composition of "shake" can vary and may have higher concentration of bud material than is desirable. Accordingly, different parts of the *Cannabis* plant, or combinations of parts of *Cannabis* plant material, can be used in the smoking process, depending upon the desired dose of *Cannabis* compounds to be deposited on the surface of the food being smoked.

Different combinations of sawdust versus *Cannabis* material may be combined for the purposes of the invention. For example, the *Cannabis* material may be as low as about 25% of the pellet used to smoke the proteinaceous food, with the remaining about 75% of the pellet being sawdust from one or more wood fuels or peat-based fuel appropriate for the smoking process. In contrast, the *Cannabis* material may comprise about 75% of the pellet and the remaining about 25% of the pellet will be sawdust from one or more wood fuels or peat-based fuel appropriate for the smoking process. Accordingly, the percentage of *Cannabis* material in the pellet may be in the range of 25% to 75%, such as about 25%, about 30%, about 35%, about 40%, about 45%, about 50%, about 55%, about 60%, about 65%, about 70%, or about 75%. The percentage of sawdust from one or more wood fuels or peat-based fuel appropriate for the smoking process will also be in the range of 75% to 25%, such that the addition of the percentage of *Cannabis* material and sawdust/peat material will result in 100%. For example, the sawdust/peat material may be about 75%, about 70%, about 65%, about 60%, about 55%, about 50%, about 45%, about 40%, about 35%, about 30%, or about 25% of the pellet.

A very broad range of *Cannabis* strains are available, with more in development due to the gradual easing of regulations surrounding research pertaining to *Cannabis*. Each variety has a different profile of active compounds. More than 480 different natural compounds are known from the *Cannabis* plant, and ongoing research promises that more such compounds will be identified over time. More than 80 of these compounds are known as cannabinoids, which are capable of binding to receptors in the human brain. The primary psychoactive compound in *Cannabis* is THC, which stands for delta-9-tetrahydrocannabinol. Other well-studied compounds from *Cannabis* include cannabidiol (CBD), cannabinol (CBN) and cannabichromene (CBC), as well as tetrahydrocannabivarin (THCV). Different *Cannabis* strains can be used in the food smoking procedure described in this invention in order to maximize the levels of the desired compound. For example, in some cases it may be preferable to minimize the level of the psychoactive THC compound, while maximizing the level of the CBD or CBN compounds. Different strains of *Cannabis* can be used to achieve the desired ratios of compounds that are deposited onto the smoked food.

The proteinaceous food product that is smoked using this technique can be vacuum-packed as described elsewhere in this disclosure. Specifically in the case of cheese, the smoked cheese product can be wrapped with food-grade wax in order to carefully preserve the *Cannabis*-derived compounds that have been deposited on the food surface. Waxing cheese is commonly practiced in order to preserve it for long periods of time and to prevent contamination. Similar waxing techniques can be used with *Cannabis*-smoked proteinaceous food products, especially cheeses. The wax that is used for waxing cheese is pliable, unlike pure paraffin wax, and will prevent mould growth while retaining moisture. Smoked cheese and other foods can also be shrink-wrapped using rapid heating techniques that do not affect the quality of the food.

Because *Cannabis* products are used for medical purposes, it is important to be able to identify the dose of cannabinoids, such as THC, contained in the *Cannabis*-smoke-infused proteinaceous foods of the invention. There are no widely-accepted precise doses or established uniform dosing schedules for *Cannabis*, in part because it is used to alleviate the symptoms of such a wide range of ailments. For example, the dose appropriate for preventing seizures in children may be very different from the dose appropriate for treating chemotherapy side-effects in adults. In addition, patients with no prior experience with *Cannabis* may require a lower dose than those who have previously used the drug. Various surveys published in the peer-reviewed scientific and medical literature have suggested that the majority of people using smoked or orally ingested marijuana for medical purposes reported using between 10-20 g of marijuana per week or approximately 1-3 g of dried marijuana per day. A large, multicenter trial used initial doses of 5 mg of oral delta-9-tetrahydrocannabinol (THC) daily, self-titrated up to 25 mg THC daily for up to 52 weeks in multiple sclerosis (Rog, D J et al. (2005) Neurology 65(6):812-189). Accordingly, it is critical that potential users of the *Cannabis*-smoke-infused proteinaceous foods of the invention understand the dosage in the product and can consume the appropriate amount given their recommended dosage as determined by their physician.

Any proteinaceous product (cheese, meat, seafood, etc.) subjected to the *Cannabis*-infused smoking procedures described above will be exposed to cannabinoids, including THC and other terpenoid compounds arising from the deposition of smoke vapours onto the surface of the proteinaceous materials.

Samples of the proteinaceous food products so created may be subjected to quantitative analysis following extraction by methods which include, and are not limited to, the following actions.

Sample preparation from *Cannabis*-infused smoking using the pulsed vacuum technique is conducted by excision of surface material in the amount of 500 mg and homogenization of said excised sample in volumes of solvent comprising, in one instance, 5 ml methanol:chloroform (9:1 v/v) by the following procedure: 10 seconds on a vortex, 15 minute ultrasonic bath, including again vortexing after 5, 10 and 15 minutes, then centrifugation. In another instance, extraction can be performed by the use of hexane solvent.

The solvent is evaporated under nitrogen gas to dryness. The residue is dissolved in 200 µl methanol:chloroform (9:1 v/v). A final solution is then prepared for analysis by dilution with methanol by a factor of up to 1,000 µl and the resulting solution is then used for analysis.

Various methods of analysis of the solution are applicable including, but not limited to, High Performance Liquid Chromatography (HPLC), Thin Layer Chromatography (TLC), and Gas Chromatography (GC). The preferred method includes the use of HPLC linked to ultraviolet detection of cannabinoids and associated semi-volatile and volatile compounds including terpenoids. In the alternate, HPLC analysis and separation linked to mass spectrometry and/or diode array for identification and quantification of inherent compounds is desirable. Volatile and semi-volatile compounds associated with cannabinoids, including terpenoids, can be separated and analyzed by use of GC linked to either mass spectrometry or diode array detection. HPLC is preferred over GC because it does not apply heat in the testing process, which allows cannabinoids to be measured in their naturally-occurring forms. Testing for cannabinoids with GC can cause acidic cannabinoids to change their structure, rendering them impossible to detect.

Smoke in the smoke/air mixture having the properties as above described, may be produced by a smoke generator 210 which may be any commercially-available smoker apparatus Examples of such smoke generators include those which may be obtained commercially from Scott Engineering, Indianapolis, Ind., U.S.A., or from KOCH Equipment L.L.C. Kansas City, Mo., U.S.A., or from AFOS Group, Hesle, England.

The smoke accumulation tank 220 is primarily connected to the vacuum-treating vessel 240 by direct smoke line 232, which may be, for example, a 3" sanitary tube with ferrules and clamps, for the introduction of smoke from the smoke accumulation tank 220. Direct smoke line 232 is provided with a smoke inlet valve V26, which may be, for example, a 3" pneumatically-operated ball valve.

The vacuum-treating vessel 240 is a generally-cylindrical hollow cylinder 242, which is oriented on in its side so that its curved faces provide an upper curved face 244 and a lower curved face 246. The interior of the vacuum-treating vessel 240 is placed under vacuum by means of vacuum pump 248. Vacuum pump 248 is connected to the interior of the vacuum-treating vessel 240 by main vacuum line 252, which may be, for example, a 3" sanitary tube with ferrules and clamps. Main vacuum line 252 is provided with vacuum-controlling valve V28, which may be, for example, a 3" pneumatically-operated ball valve.

Vacuum-treating vessel 240 is provided fresh air inlet valve V30 which may be, for example, a 3" pneumatically-operated ball valve which is installed in connecting line 290 through the upper curved face 242 of vacuum-treating vessel 240. The vacuum-treating vessel 240 is also provided with vacuum gauge 254 which is fitted to connecting line 292 through the upper curved face 242 of the vacuum-treating vessel 240 to provide information on the vacuum within the vacuum-treating vessel 240.

Smoke/air mixture is admitted to the interior of the vacuum-treating vessel 240 via bifurcated upcomer smoke line 258 through its connection to direct smoke line 232. Bifurcated upcomer smoke line 258 is enters the vacuum-treating vessel 240 through the lower curved face 244 of the vacuum-treating vessel 240 by way of a suitable line 260 from the smoke accumulation tank 220.

The vacuum-treating vessel 240 is placed under sealed vacuum conditions. Thus, the vacuum-treating vessel 240 is placed under suitable sub-atmospheric pressure, which may be, for example within the range of about 20 inches of Hg to about 29 inches of Hg, desirably from 22 inches of Hg to 29 inches of Hg and preferably from 26 inches of Hg to 29 inches of Hg (respectively, from about 515 mm Hg to about 735 mm Hg, desirably from about 565 mm of Hg to about 735 mm Hg and preferably from about 670 mm of Hg to about 735 mm Hg). The vacuum-treating vessel 240 includes two vacuum-tight sealable closure doors, namely ingress door 262 and egress door 264, which are supported on door supports 276, 278, respectively. As shown, (see FIG. 3) ingress door 262 is in its vacuum-sealed condition, while egress door 264 is shown in its open condition.

The control valves V22, V24, V26, V28 and V30 are controlled by controls 250. These controls 250 may be by manual timing means, but are preferably programmable controls 250 which may be, e.g., an Allen Bradley Micrologic 1000™ Programmable Controller.

The loading of the vacuum-treating vessel 240 with the selected proteinaceous food product is by means of a hinged loading stand 280. As shown, (see FIG. 3) the hinged loading stand 280 has its hinged section 282 in its "up" condition. The unloading of the vacuum-treating vessel 240 with the thus-smoke infused selected proteinaceous food product is through hinged section 264 onto product racks 268, which are supported on discharge stand 270. The unloaded smoke infused selected proteinaceous food product is transported by suitable means to a "cold" room for a chill resting cycle. The chill resting cycle is desirably at a temperature of between about 0° C. to about 6° C., preferably between about 2° C. and about 4° C. of such smoke-infused proteinaceous foods for a suitable period of time; e.g. at least about 1 hour and preferably 5 hours or more, e.g., between about 6 and about 10 hours.

Summary of Apparatus Units

The vacuum-treating vessel 240 holds the proteinaceous food product to be smoked. b) The accumulation tank 220 stores the smoke from the smoke generator 210. c) The smoke generator 210 produces smoke and feeds it to the accumulation tank 220 via a blower (not seen). d) The vacuum pump 246 removes air from the vacuum-treating vessel 240. e) Pneumatically-operated control valves are V22, V24, V26, V28, and V30. f) Valve V22 (normally open) is between the smoke accumulation tank 220 and the smoke generator 210. g) Valve V24 (normally open) is between the smoke generator 210 and the smoke accumulation tank 220. h) Valve V26 (normally closed) is between the vacuum-treating vessel 240 and the smoke accumulation tank 220. i) V28 valve (normally closed) is between the vacuum-treating vessel 240 and the vacuum pump 246. j) V30 valve (normally closed) is between the vacuum chamber 246 and ambient exterior. k) Pneumatically-operated control valves V22, V24, V26, V28 and V30 are actuated by solenoid valves controlled by an Allen Bradley Micrologic 1000™ Programmable Controller.

Summary of Operation

In operation, the proteinaceous food product is placed into the vacuum-treating vessel 240 and the two vacuum-tight sealable closure doors, namely ingress door 262 and egress door 264, are closed. The operator turns on the controller 250 and, by computer prompts, sets the number of cycles required for proper smoking of the particular proteinaceous food product. Control valves V26, V28 & V30 are closed. Smoke generator 210 produces an air/smoke mixture and fills the smoke accumulation tank 220. Both control valves V22 & V24 are open, thus allowing the air/smoke mixture to fill the accumulation tank 220 and to re-circulate back through the smoke generator to increase the smoke density, aided by the blower (not seen). When the operator presses "start" on the controller 250, control valve V28 opens and air is drawn from the two vacuum-tight sealable closure doors, namely ingress door 262 and egress door 264. This control valve V28 remains open until the preset vacuum reaches the above-described values. At that point, control valve V28 as well as control valves V22 & V24 that isolate the smoke generator 210 from the accumulation tank 220 close. Then control valve V26 opens and smoke from the accumulation tank 240 is draw into the vacuum-treating vessel 240. When the vacuum-treating vessel 240 reaches atmospheric pressure, control valve V26 closes and control valves V22 & V24 open. This completes one cycle of the 50 to about 400 cycles.

The process repeats itself until it reaches the number of cycles set by the operator. At that point, control valve V28 opens and air is drawn from the vacuum-treating vessel 240. Control valve V28 remains open until the above-recited preset vacuum is reached. At that point control valve V28 closes and control valve V30 opens to allow fresh air to be drawn into the vacuum-treating vessel 240. At a preset time, control valve V30 closes.

In the case of using smoke that includes *Cannabis*-derived compounds, the number of cycles can be varied in order to produce a mild, medium, or strong flavoured product. The mild flavoured product has the smallest amount of *Canna-* bis-derived compounds deposited on the surface, while the strong flavoured product has the largest amount of *Cannabis*-derived compounds deposited on the surface. Increasing the number of cycles exposes the product to increasing amounts of smoke and allows for increased time for the *Cannabis*-derived compounds to be deposited on the surface of the food. In order to produce the mild flavoured product, about 50-150 cycles would be used. In order to produce a medium flavoured product, about 150 to 300 cycles would be used. In order to produce a strong flavoured product, about 300 to 400 cycles would be used. The strength of the flavour will also be dependent upon the strain or variety of *Cannabis* used in the smoke fuel. Individual varieties can be tested empirically for flavour characteristics and intensity.

Now the programmed 50 to about 400 cycles are complete. The operator can open ingress door 262 and egress door 264, and remove the smoked proteinaceous food product from the vacuum-treating vessel 240.

Operation and Generic Example

A generic method of the present invention using the apparatus as above described in FIG. 2, FIG. 3, FIG. 4 and FIG. 5 is as follows.

The selected proteinaceous foods, e.g., cheese, crustacean, e.g., lobster, bivalve mollusk, e.g., oyster, gastropod mollusk, e.g., abalone, fish, e.g., salmon, meat, e.g., brisket or poultry, e.g. turkey breast, are smoke-infused using the apparatus described in FIG. 2, FIG. 3, FIG. 4 and FIG. 5. Pieces of the selected proteinaceous food, to be smoke-infused are placed in desired proportions on product racks 268 and are then introduced into the interior of the vacuum vessel 240. Vacuum pump 246 removes air from the interior of the vacuum vessel 240 to create a vacuum of the order of about 20 inches of Hg to about 29 inches of Hg, desirably from 22 inches of Hg to 29 inches of Hg and preferably from 26 inches of Hg to 29 inches of Hg (respectively, from about 515 mm Hg to about 735 mm Hg, desirably from about 565 mm of Hg to about 735 mm of Hg and preferably from about 670 mm of Hg to about 735 mm Hg), within the vacuum vessel 240. The operation of the vacuum pump 234 is then stopped. The air/smoke mixture which has moisture content of about 10% to about 50% by weight which is prepared as described above and is first held in smoke accumulation tank 220 and recycled to provide a concentration of smoke which may be up to about 50%, is then controllably transferred from the accumulation tank 220 to the interior of the vacuum-treating vessel 240 through bifurcated upcomer 258 by opening smoke control valve V21 until equilibrium is reached, within about 10 to about 30 seconds. Once the vacuum vessel 240 becomes filled with smoke, i.e., when an atmosphere of smoke is created within the vacuum vessel 240, the smoke infuses rapidly into the proteinaceous food product. The transfer of the air/smoke mixture from the accumulation tank 220 to the interior of the vacuum vessel 240 is then discontinued and vacuum pump 246 is again actuated to withdraw smoke which had not infused into the proteinaceous food product from the vacuum-treating vessel 240. This reduces the negative pressure within the vacuum smoke-infusing compartment to the above specified negative pressure level These method steps are repeated so that new or recycled smoke always refilled the vacuum vessel 240.

Control valves V22, V24, V26, V28 and V30 are controllably operated as fully described above. The opening of vacuum release and fresh air valve V28 removes smoke which had not been perfused into the proteinaceous food product and brings the vacuum vessel 240 up to atmospheric pressure.

These pulsed sequences of smoke introduction stage/vacuum purging stage/vacuum release stage is periodically repeated, i.e., smoke introduction stage for about 1 to about 10 seconds, vacuum purging stage for about 5 to about 30 seconds and vacuum release stage for about 1 to about 10 seconds for about 50 to about 400 cycles. The sequence of opening/closing of control valves V22, V24, V26, V28 and V30 may be actuated manually, but are preferably automatically controlled by controls 250 which is, e.g., an Allen Bradley Micrologic 1000™ Programmable Controller.

In order to remove the selected smoke-infused proteinaceous food from the vacuum vessel 240, vacuum release and fresh air valve V23 is opened to return the vacuum vessel 240 back to atmospheric pressure.

The method is controlled to operate under the following conditions: Vacuum: about 20 inches of Hg to about 29 inches of Hg, desirably from 22 inches of Hg to 29 inches of Hg and preferably from 26 inches of Hg to 29 inches of Hg (respectively from about 515 mm Hg to about 735 mm Hg, desirably from about 565 mm of Hg to about 735 mm Hg and preferably from about 670 mm of Hg to about 735 mm Hg). Smoke introduction stage for about 1 to about 10 seconds Vacuum purging stage for about 5 to about 30 seconds Vacuum release stage for about 1 to about 10 seconds Number of cycles: 50 to about 400 cycles When the selected proteinaceous food within the vacuum vessel 240 was adequately smoke-infused, such selected smoke-infused proteinaceous food was removed. The removed selected smoke-infused proteinaceous food was subjected to the additional essential step of chilled resting. The removed selected smoke-infused proteinaceous food was transported by suitable means into a cold room. For example, they may be transported on the product racks 268 manually into the cold room A cold resting cycle is then carried out at a temperature of about 2° C. to about 4° C. to remain there for a period of at least 1 hour, i.e. about 5 hours to about 8 hours, e. g., about 6 hours, to provide a chilled rested selected smoke-infused proteinaceous food. Alternatively, the removed smoke-infused proteinaceous food product may be discharged from the product racks 268 directly onto a conveyor belt (not shown) and are then conveyed into a cold room as above specified, at a temperature of about 2° C. to about 4° C. to remain there for a period of about 6 hours, to provide a chilled rested smoke-infused proteinaceous food product. Thus, the chilled resting cycle was desirably from about 1 to about 6 hours at about 1° C. to about 6° C.

Example 1

Cheeses may be smoke-infused according to one embodiment of the method of the present invention. The smoke-infusing method on cheddar cheese according to an embodiment of this invention, was carried out as described below.

Pieces of the cheddar cheese as to be smoke-infused were placed in desired proportions on trays within the interior of the vacuum vessel as previously defined in FIG. 2, FIG. 3, FIG. 4 and FIG. 5. The vacuum vessel was then sealed. The vacuum pump as previously defined was operated as previously defined to create a negative pressure within the vacuum-treating vessel of the order of about 26 inches of Hg to 29 inches of Hg (from about 670 mm of Hg to about 735 mm Hg), i.e., at or nearly at full vacuum. Smoke having an increased smoke content which had been provided by the above-described recycling, and which was initially had a smoke/air mixture moisture content of about 10% to about 50%, by weight was then admitted into the vacuum-treating vessel until equilibrium was reached. Smoke introduction was then ceased and substantially simultaneously vacuum was applied. The smoke infusion took place at a suitable low temperature e.g., of about 4° C. for a time of about 2 to 20 seconds. This then removed smoke which had not been perfused into the cheddar cheese to be smoke-infused was removed. This sequence of method steps, i.e., introducing smoke into the vacuum-treating zone, and then removing the smoke was repeated 50 to about 400 times, i.e., in pulsed sequences of smoke introduction stage/vacuum purging stage/vacuum release stage which results in the efficient infusion of smoke into the cheddar cheese. This pulsed sequence of smoke introduction stage/vacuum purging stage/vacuum release stage was periodically repeated, as above noted, i.e., smoke introduction stage for about 1 to about 10 seconds, vacuum purging stage for about 5 to about 30 seconds and vacuum release stage for about 1 to about 10 seconds for about 50 to about 400 cycles. In order to remove the smoke-infused cheddar cheese from the vacuum vessel fresh air was introduced to bring the vacuum vessel to atmospheric pressure.

The smoke-infused cheddar cheese was removed. An empirical test was performed to assess the odor and taste of the smoke-infused cheddar cheese. It was found that such cheese had a smoky acrid aroma and an unpleasant smoky taste.

Thus, the procedure is controlled to be carried out as follows: Vacuum: about 26 inches of Hg to about 29 inches of Hg (from about 670 mm of Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles The removed smoke-infused cheddar cheese was subjected to the additional essential step of a chilled resting cycle as previously described in the cold room at a temperature of about 2° C. to about 6° C. for a period of about 6 hours. Thus, the chilled resting cycle was about 1 to about 6 hours at about 2° C. to about 6° C.

The smoke-infused cheddar cheese which had been prepared by the smoke-infusion method of an aspect of the present invention as described above and which included the above-described essential step of the chilled resting cycle as above specified was again subjected to the empirical test to assess the odor and taste of the smoke-infused cheddar cheese. It was found that such cheese had no substantial smoky aroma, had improved acceptably-mild smoky taste and had improved preservation qualities.

Example 2

The method as described for the production of smoke-infused cheddar cheese is modified for the production of smoke-infused Gouda cheese. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke-infused Gouda cheese which is prepared according to the above-described method steps of the present invention has no substantial smoky aroma, has improved acceptably-mild smoky taste and has improved preservation qualities.

Example 3

The method as described for the production of smoke-infused cheddar cheese is modified for the production of smoke-infused Colby cheese. The procedure is controlled to be carried out as follows: Vacuum: about 20 inches of Hg to about 29 inches of Hg (about 515 mm Hg to about 735 mm Hg). Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke-infused Colby cheese which is prepared according to the above-described method steps of the present invention, has no substantial smoky aroma, has improved acceptably-mild smoky taste and has improved preservation qualities.

Example 4

The method as described for the production of smoke-infused cheddar cheese, is modified for the production of smoke-infused Gruyere cheese. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke-infused Gruyere cheese which is prepared according to the above-described method of the present invention, has no substantial smoky aroma, has improved acceptably-mild smoky taste and has improved preservation qualities.

The method of aspect of this invention may be carried out with equally-effective results on at least all the cheeses specifically-listed hereinabove.

Example 5

The smoke-infusing method on a crustacean i.e. lobsters according to an embodiment of this invention, was carried out as described below.

American or Canadian cold water clawed lobsters were separated from the shell by usual means, e.g., by the method described in U.S. Pat. No. 6,159,528 patented Dec. 12, 2000 by Gallant et al, (the entire contents of which are hereby incorporated by reference), which provided methods for separating the intact shell of hard-shelled crustaceans from the raw edible meat contained therein which is very strongly attached to the shells by specified freeze-thaw cycles. The so-separated meat is subjected to the method of the present invention under the method conditions previously described in detail.

Pieces of the separated meat of the lobster as so-described to be smoke-infused were placed in desired proportions on trays within the interior of the vacuum vessel as previously defined in FIG. 2, FIG. 3, FIG. 4 and FIG. 5. The vacuum vessel was then sealed. The vacuum pump as previously defined was operated as previously defined to create a negative pressure within the vacuum-treating vessel of the order of about 26 inches of Hg to 29 inches of Hg (from about 670 mm of Hg to about 735 mm Hg), i.e., at or nearly at full vacuum. Smoke having an increased smoke content which had been provided by the above-described recycling procedure, and which initially had a smoke/air mixture moisture content of about 10% to about 50%, by weight, was then admitted into the vacuum-treating vessel until equilibrium was reached. Smoke introduction was then ceased and substantially simultaneously vacuum was applied. The smoke infusion took place at a suitable low temperature of e.g., about 4° C. for a time of about 2 to 20 seconds. By this procedure, smoke which had not been perfused into the lobster meat to be smoke-infused was removed. This sequence of method steps, i.e., introducing smoke into the vacuum-treating zone, and then removing the smoke was repeated 50 to about 400 times, i.e., in pulsed sequences of smoke introduction stage/vacuum purging stage/vacuum release stage which results in the efficient infusion of smoke into the lobster meat. This pulsed sequence of smoke introduction stage/vacuum purging stage/vacuum release stage was periodically repeated, as above noted, i.e., smoke introduction stage for about 1 to about 10 seconds, vacuum purging stage for about 5 to about 30 seconds and vacuum release stage for about 1 to about 10 seconds for about 50 to about 400 cycles. In order to be able to remove the smoke-infused lobster meat from the vacuum vessel fresh air was introduced to bring the vacuum vessel to atmospheric pressure.

The smoke-infused lobster meat was then removed. An empirical test is performed to assess the odor and taste of the smoke-infused lobster meat. It was found that such lobster meat had a smoky acrid aroma and an unpleasant smoky taste.

Thus, the procedure was controlled to be carried out as follows: Vacuum: about 26 inches of Hg to about 29 inches of Hg (from about 670 mm of Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles The removed smoke-infused lobster meat was subjected to the additional essential step of a chilled resting cycle as previously described in the cold room at a temperature of about 2° C. to about 6° C. for a period of about 6 hours. Thus, the chilled resting cycle was about 1 to about 6 hours at about 2° C. to about 6° C.

The smoke-infused lobster meat which had been prepared by the smoke-infusion method of an aspect of the present invention as described above and which included the above-described essential step of the chilled resting cycle as above specified was again subjected to the empirical test to assess the odor and taste of the smoke-infused lobster meat. It was found that such lobster meat had no substantial smoky aroma, had improved acceptably-mild smoky taste and had improved preservation qualities.

While the above smoke infusion has been described for extracted lobster meat, it is equally applicable to the following lobster smoke infusions:

The lobster shell may be scored and the entire lobster may be subjected to the smoke infusion; i.e, below the lobster shell.

The lobster claws may be separated from the entire lobster, then scored and the scored lobster claws may be subjected to the smoke infusion; below the lobster claw shell.

The lobster tails may be separated from the entire lobster, then scored and the scored lobster tails may be subjected to the smoke infusion; below the lobster tail shell.

The whole lobster may be eviscerated and the whole eviscerated lobster may be subjected to the smoke infusion.

Example 6

The method as described above for the production of smoke-infused lobster is modified for the production of smoke-infused snow crab. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The snow crab which was smoke infused according to the above-described method of the present invention, has no substantial smoky aroma, has improved acceptably-mild smoky taste and has improved preservation qualities.

Example 7

The method as described above for the production of smoke-infused lobster is modified for the production of smoke-infused King crab. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The King crab which was smoke infused according to the above-described method of the present invention, has no substantial smoky aroma, has improved acceptably-mild smoky taste and has improved preservation qualities.

Example 8

The method as described above for the production of smoke-infused lobster is modified for the production of smoke-infused, raw, fresh shell-on common shrimp. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles Chilled resting period: about 1 to about 6 hours at about 1° C. to about 6° C.

The smoke-infused raw, fresh shell-on common shrimp prepared according to the above-described method of the present invention has an easily-removable shell, has no substantial smoky aroma, has improved acceptably-mild smoky taste and has improved preservation at ordinary freezing temperatures.

Example 9

The method as described above for the production of smoke-infused common shrimp is modified for the production of smoke-infused raw, fresh shell-on prawns. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles Chilled resting period: about 1 to about 6 hours at about 1° C. to about 6° C.

The smoke-infused raw, fresh shell-on prawns prepared according to the above-described method of the present invention, has an easily-removable shell, has no substantial smoky aroma, has improved acceptably-mild smoky taste and has improved preservation at ordinary freezing temperatures.

The method of aspect of this invention may be carried out with equally-effective results on at least all the crustaceans specifically-listed hereinabove.

Example 10

The smoke-infusing method on intact oysters according to an embodiment of this invention, was carried out as described below.

Intact oysters to be smoke-infused were placed on trays within the interior of the vacuum vessel as previously described in FIG. 2, FIG. 3, FIG. 4 and FIG. 5. The vacuum vessel was then sealed. The vacuum pump as previously defined was operated as previously defined to create a negative pressure of the order of about 26 inches of Hg to 29 inches of Hg (from about 670 mm of Hg to about 735 mm Hg), i.e., at or nearly at full vacuum, within the vacuum-treating vessel. Smoke which had an increased smoke content which had been provided by the above-described recycling, and which had a smoke/air mixture moisture content of about 10% to about 50% by weight, was then admitted into the vacuum-treating vessel until equilibrium was reached. Smoke introduction was then ceased and substantially simultaneously vacuum was applied. The smoke infusion took place at a suitable low temperature of e.g., about 4° C. for a time of about 2 to 20 seconds. Smoke which had not been perfused into the oysters to be smoke-infused was removed. This sequence of steps, i.e., introducing smoke into the vacuum-treating zone, and then removing the smoke was repeated 50 to about 400 times i.e., in pulsed sequences of smoke introduction stage/vacuum purging stage/vacuum release stage which results in the efficient infusion of smoke into the intact oysters. This pulsed sequences of smoke introduction stage/vacuum purging stage/vacuum release stage was periodically repeated, as above noted, i.e., smoke introduction stage for about 1 to about 10 seconds, vacuum purging stage for about 5 to about 30 seconds and vacuum release stage for about 1 to about 10 seconds for about 50 to about 400 cycles. In order to remove the smoke-infused intact oysters from the vacuum vessel fresh air was introduced to bring the vacuum vessel to atmospheric pressure.

The method for the production of smoke-infused intact oysters, is controlled to be carried out as follows: Vacuum: about 26 inches of Hg to about 29 inches of Hg (from about 670 mm of Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles The smoke-infused intact oysters were removed. An empirical test was performed to assess the odor and taste of the smoke-infused oysters. It was found that such intact oysters had a smoky acrid aroma and an unpleasant smoky taste. The removed smoke-infused intact oysters were now subjected to the essential step of a chill resting cycle at about 1 to about 6 hours at about 1° C. to about 6° C. Thus the chilled resting cycle was at about 1 to about 6 hours at about 1° C. to about 6° C.

The smoke-infused intact oysters which were prepared according to the above-described method steps of the present invention including the essential step of the chill resting cycle were now subjected to an empirical test to assess the odor and taste of the smoke-infused intact oysters. It is found that such smoke-infused intact oysters were surprisingly still alive, easily removable from their shells, had no substantial smoky aroma, had improved acceptably-mild smoky taste and had improved preservation at ordinary refrigeration temperature.

Example 11

The method as described above for the production of smoke-infused intact oysters was modified for the production of smoke-infused intact hard shell clams (quahogs). The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: about 50 to about 400 cycles Chilled resting cycle: about 1 to about 6 hours at about 1° C. to about 6° C.

The smoke infused intact common hard shell clams (quahogs) prepared according to the above-described method of the present invention, are surprisingly still alive, are easily removable from their shells, have no substantial smoky aroma and have improved acceptably-mild smoky taste and preservation at ordinary refrigeration temperature.

Example 12

The method as described above for the production of smoke-infused oysters is modified for the production of live, intact shell-on smoke-infused razor clams is carried out. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke-infused intact razor clams which have been prepared according to the above-described method steps of the present invention, are surprisingly still live, may be easily removable from their shells and have improved delicate smoke taste, smell and preservation at ordinary refrigeration temperature.

Example 13

The method as described above for the production of smoke-infused oysters is modified for the production of live, intact shell-on smoke-infused mussels. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: about 50 to about 400 cycles Chilled resting period: about 1 to about 6 hours at about 1° C. to about 6° C.

The smoke infused intact mussels prepared according to the above-described method of the present invention, have no substantial smoky aroma have improved acceptably-mild smoky taste and have improved taste and preservation at ordinary refrigeration temperature.

When the smoke infused intact mussels are encased in a vacuum bag, cooked and then frozen, and when they are thawed and removed from the vacuum bag, they may be easily removable from their shell.

Example 14

The method as described above for the production of smoke-infused oysters is modified for the production of smoke-infused adductor muscle of scallops. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: about 50 to about 400 cycles Chilled resting period: about 1 to about 6 hours at about 1° C. to about 6° C.

The smoke infused adductor muscle of the scallops prepared according to the above-described method of the present invention, has no substantial smoky aroma, has improved acceptably-mild smoky taste and preservation at ordinary refrigeration temperature.

The method of aspect of this invention may be carried out with equally-effective results on at least all the bivalve mollusks specifically-listed hereinabove.

Example 15

The method as described above for the production of smoke-infused oysters is modified for the production of smoke-infused muscle tissue of abalone. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: about 150 to about 200 cycles Chilled resting cycle: about 1 to about 6 hours at about 1° C. to about 6° C.

The smoke infused muscle tissue of abalones prepared according to the above-described method of the present invention, has no substantial smoky aroma, has improved acceptably-mild smoky taste and preservation at ordinary refrigeration temperature.

The method of aspect of this invention may be carried out with equally-effective results on at least all the gastropod mollusks specifically-listed hereinabove.

Example 16

The method as described above for the production of smoke-infused oysters is modified for the production of smoke-infused octopus meat from any part of the octopus. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: about 50 to about 400 cycles Chilled resting cycle: about 1 to about 6 hours at about 1° C. to about 6° C.

The smoke infused octopus meat prepared according to the above-described method of the present invention, has no substantial smoky aroma, has improved acceptably-mild smoky taste and enhanced preservation at ordinary refrigeration temperature.

The method of aspect of this invention may be carried out with equally-effective results on at least all the cephalid mollusks specifically-listed hereinabove.

Example 17

Fish may be smoke-infused according to one embodiment of the method of the present invention. One example of the smoke-infusing method on Arctic char which may be smoke-infused, according to this invention is now described.

Pieces of the Arctic char or whole Arctic char, to be smoke-infused are placed in desired proportions on trays within the interior of the vacuum vessel as previously described in FIG. 2, FIG. 3, FIG. 4 and FIG. 5. The vacuum vessel is then sealed. The vacuum pump as previously defined was operated as previously defined to create a negative pressure within the vacuum-treating vessel of the order of about 26 inches of Hg to 29 inches of Hg (from about 670 mm of Hg to about 735 mm Hg), i.e., at or nearly at full vacuum. Smoke having an increased smoke content which had been provided by the above-described recycling, and which was initially had a smoke/air mixture moisture content of about 10% to about 50%, by weight was then admitted into the vacuum-treating vessel until equilibrium was reached. Smoke introduction was then ceased and substantially simultaneously vacuum was applied. The smoke infusion took place at a suitable low temperature of e.g., about 4° C. for a time of about 2 to 20 seconds. This then removed smoke which had not been perfused into the Arctic char to be smoke-infused was removed. This sequence of method steps, i.e., introducing smoke into the vacuum-treating zone, and then removing the smoke was repeated 50 to about 400 times, i.e., in pulsed sequences of smoke introduction stage/vacuum purging stage/vacuum release stage which results in the efficient infusion of smoke into the Arctic char This pulsed sequences of smoke introduction stage/vacuum purging stage/vacuum release stage was periodically repeated, as above noted, i.e., smoke introduction stage for about 1 to about 10 seconds, vacuum purging stage for about 5 to about 30 seconds and vacuum release stage for about 1 to about 10 seconds for about 50 to about 400 cycles. In order to remove the smoke-infused Arctic char from the vacuum vessel fresh air was introduced to bring the vacuum vessel to atmospheric pressure.

The smoke-infused Arctic char was removed. An empirical test was performed to assess the odor and taste of the smoke-infused Arctic char. It was found that such Arctic char had a smoky acrid aroma and an unpleasant smoky taste.

Thus, the procedure is controlled to be carried out as follows: Vacuum: about 26 inches of Hg to about 29 inches of Hg (from about 670 mm of Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles The removed smoke-infused Arctic char was subjected to the additional essential step of a chilled resting cycle as previously described in the cold room at a temperature of about 2° C. to about 6° C. for a period of about 6 hours. Thus, the chilled resting cycle was about 1 to about 6 hours at about 2° C. to about 6° C.

The smoke-infused Arctic char which had been prepared by the smoke-infusion method of an aspect of the present invention as described above and which included the above-described essential step of the chilled resting cycle as above specified was again subjected to the empirical test to assess the odor and taste of the smoke-infused Arctic char. It was found that such Arctic char had no substantial smoky aroma, had improved acceptably-mild smoky taste and had improved preservation qualities.

Example 18

The method as described above for the production of smoke-infused Arctic char is modified for the production of smoke-infused salmon. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused salmon prepared according to the above-described method of the present invention, has no substantial smoky aroma, has improved acceptably-mild smoky taste and has enhanced preservation at ordinary refrigeration temperature.

Example 19

Pieces of trout or whole trout is/are subjected to the method of the present invention under modified method conditions for smoke infusing Arctic char as previously described in detail. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused trout prepared according to the above-described method of the present invention, has no substantial smoky aroma, has improved acceptably-mild smoky taste and has enhanced preservation at ordinary refrigeration temperature The method of aspect of this invention may be carried out with equally-effective results on at least all the fish specifically-listed hereinabove.

Example 20

Various meats may be smoke-infused according to one embodiment of the method of the present invention. One example of the smoke-infusing method on various meats is on beef brisket which may be smoke-infused, according to this invention is now described.

Pieces of the brisket to be smoke-infused are placed in desired proportions on trays within the interior of the vacuum vessel as previously described in FIG. 2, FIG. 3, FIG. 4 and FIG. 5. The vacuum vessel is then sealed. The vacuum pump as previously defined was operated as previously defined to create a negative pressure within the vacuum-treating vessel of the order of about 26 inches of Hg to 29 inches of Hg (from about 670 mm of Hg to about 735 mm Hg), i.e., at or nearly at full vacuum. Smoke having an increased smoke content which had been provided by the above-described recycling, and which was initially had a smoke/air mixture moisture content of about 10% to about 50%, by weight was then admitted into the vacuum-treating vessel until equilibrium was reached. Smoke introduction was then ceased and substantially simultaneously vacuum was applied. The smoke infusion took place at a suitable low temperature of e.g., about 4° C. for a time of about 2 to 20 seconds. This then removed smoke which had not been perfused into the beef brisket to be smoke-infused was removed. This sequence of method steps, i.e., introducing smoke into the vacuum-treating zone, and then removing the smoke was repeated 50 to about 400 times, i.e., in pulsed sequences of smoke introduction stage/vacuum purging stage/vacuum release stage which results in the efficient infusion of smoke into the beef brisket. This pulsed sequences of smoke introduction stage/vacuum purging stage/vacuum release stage was periodically repeated, as above noted, i.e., smoke introduction stage for about 1 to about 10 seconds, vacuum purging stage for about 5 to about 30 seconds and vacuum release stage for about 1 to about 10 seconds for about 50 to about 400 cycles. In order to remove the smoke-infused beef brisket from the vacuum vessel fresh air was introduced to bring the vacuum vessel to atmospheric pressure.

The smoke-infused beef brisket was removed. An empirical test was performed to assess the odor and taste of the smoke-infused beef brisket. It was found that such beef brisket had a smoky acrid aroma and an unpleasant smoky taste.

Thus, the procedure is controlled to be carried out as follows: Vacuum: about 26 inches of Hg to about 29 inches of Hg (from about 670 mm of Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles The removed smoke-infused beef brisket was subjected to the additional essential step of a chilled resting cycle as previously described in the cold room at a temperature of about 2° C. to about 6° C. for a period of about 6 hours. Thus, the chilled resting cycle was about 1 to about 6 hours at about 2° C. to about 6° C.

The smoke-infused beef brisket which had been prepared by the smoke-infusion method of an aspect of the present invention as described above and which included the above-described essential step of the chilled resting cycle as above specified was again subjected to the empirical test to assess the odor and taste of the smoke-infused beef brisket. It was found that such beef brisket had no substantial smoky aroma, had improved acceptably-mild smoky taste and had improved preservation qualities.

Example 21

The method as described above for the production of smoke-infused beef brisket is modified for the production of smoke-infused veal breast. The procedure is controlled to be carried out as follows: Vacuum: about 20 inches of Hg to about 29 inches of Hg (about 515 mm Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused veal breast prepared according to the above-described method of the present invention, has no substantial smoky aroma, has improved acceptably-mild smoky taste and has enhanced preservation at ordinary refrigeration temperature.

Example 22

The method as described above for the production of smoke-infused beef brisket is modified for the production of smoke-infused ham. The procedure is controlled to be carried out as follows: Vacuum: about 20 inches of Hg to about 29 inches of Hg (about 515 mm Hg to about 735 mm Hg). Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused ham prepared according to the above-described method of the present invention, has no substantial smoky aroma, has improved acceptably-mild smoky taste and has enhanced preservation at ordinary refrigeration temperature.

Example 23

The method as described above for the production of smoke-infused beef brisket is modified for the production of smoke-infused pork belly for the production of pork bacon. The procedure is controlled to be carried out as follows: Vacuum: about 20 inches of Hg to about 29 inches of Hg (about 515 mm Hg to about 735 mm Hg). Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused bacon prepared according to the above-described method of the present invention, has no substantial smoky aroma, has improved acceptably-mild smoky taste and has enhanced preservation at ordinary refrigeration temperature.

Example 24

The method as described above for the production of smoke-infused beef brisket is modified for the production of smoke-infused minced pork sausage meat, which includes minced pork, cereal and spices. The procedure is controlled to be carried out as follows: Vacuum: about 20 inches of Hg to about 29 inches of Hg (about 515 mm Hg to about 735 mm Hg). Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused minced pork sausage meat prepared according to the above-described method of the present invention, has no substantial smoky aroma, has improved acceptably-mild smoky taste and has enhanced preservation at ordinary refrigeration temperatures.

In addition, sausages prepared from such smoke infused minced pork sausage meat can be made into sausages having enhanced flavour with less salt therein.

Example 25

The method as described above for the production of smoke-infused beef brisket is modified for the production of smoke-infused minced sheep or lamb meat. The procedure is controlled to be carried out as follows: Vacuum: about 20 inches of Hg to about 29 inches of Hg (about 515 mm Hg to about 735 mm Hg). Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused sheep or lamb minced meat prepared according to the above-described method of the present invention, has no substantial smoky aroma, has improved acceptably-mild smoky taste and has enhanced preservation at ordinary refrigeration temperature.

Example 26

The method as described above for the production of smoke-infused beef brisket is modified for the production of smoke-infused venison. The procedure is controlled to be carried out as follows: Vacuum: about 20 inches of Hg to about 29 inches of Hg (about 515 mm Hg to about 735 mm Hg). Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused venison prepared according to the above-described method of the present invention, has no substantial smoky aroma, has improved acceptably-mild smoky taste and has enhanced preservation at ordinary refrigeration temperature.

Example 27

The method as described above for the production of smoke-infused beef brisket is modified for the production of smoke-infused goat short loin. The procedure is controlled to be carried out as follows: Vacuum: about 20 inches of Hg to about 29 inches of Hg (about 515 mm Hg to about 735 mm Hg). Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused goat short loin prepared according to the above-described method of the present invention, has no substantial smoky aroma, has improved acceptably-mild smoky taste and has enhanced preservation at ordinary refrigeration temperature.

The method of aspects of this invention may be carried out with equally-effective results on at least all the meats specifically-listed hereinabove.

Example 28

Poultry may be smoke-infused according to one embodiment of the method of the present invention. One example of the smoke-infusing method of poultry is on turkey breast which may be smoke-infused, according to this invention is now described.

Pieces of the turkey breast to be smoke-infused are placed in desired proportions on trays within the interior of the vacuum vessel as previously described in FIG. 2, FIG. 3, FIG. 4 and FIG. 5 The vacuum vessel is then sealed. The vacuum pump as previously defined was operated as previously defined to create a negative pressure within the vacuum-treating vessel of the order of about 26 inches of Hg to 29 inches of Hg (from about 670 mm of Hg to about 735 mm Hg), i.e., at or nearly at full vacuum. Smoke having an increased smoke content which had been provided by the above-described recycling, and which was initially had a smoke/air mixture moisture content of about 10% to about 50%, by weight was then admitted into the vacuum-treating vessel until equilibrium was reached. Smoke introduction was then ceased and substantially simultaneously vacuum was applied. The smoke infusion took place at a suitable low temperature of e.g., about 4° C. for a time of about 2 to 20 seconds. This then removed smoke which had not been perfused into the turkey breast to be smoke-infused was removed. This sequence of method steps, i.e., introducing smoke into the vacuum-treating zone, and then removing the smoke was repeated 50 to about 400 times, i.e., in pulsed sequences of smoke introduction stage/vacuum purging stage/vacuum release stage which results in the efficient infusion of smoke into the turkey breast. This pulsed sequences of smoke introduction stage/vacuum purging stage/vacuum release stage was periodically repeated, as above noted, i.e., smoke introduction stage for about 1 to about 10 seconds, vacuum purging stage for about 5 to about 30 seconds and vacuum release stage for about 1 to about 10 seconds for about 50 to about 400 cycles. In order to remove the smoke-infused turkey breast from the vacuum vessel fresh air was introduced to bring the vacuum vessel to atmospheric pressure.

The smoke-infused turkey breast was removed. An empirical test was performed to assess the odor and taste of the smoke-infused turkey breast. It was found that such turkey breast had a smoky acrid aroma and an unpleasant smoky taste.

Thus, the procedure is controlled to be carried out as follows: Vacuum: about 26 inches of Hg to about 29 inches of Hg (from about 670 mm of Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles The removed smoke-infused turkey breast was subjected to the additional essential step of a chilled resting cycle as previously described in the cold room at a temperature of about 2° C. to about 6° C. for a period of about 6 hours. Thus, the chilled resting cycle was about 1 to about 6 hours at about 2° C. to about 6° C.

The smoke-infused turkey breast which had been prepared by the smoke-infusion method of an aspect of the present invention as described above and which included the above-described essential step of the chilled resting cycle as above specified was again subjected to the empirical test to assess the odor and taste of the smoke-infused turkey breast. It was found that such turkey breast had no substantial smoky aroma, had improved acceptably-mild smoky taste and had improved preservation qualities.

Example 29

The method as described above for the production of smoke-infused turkey breast is modified for the production of smoke-infused chicken drum sticks. The procedure is controlled to be carried out as follows: Vacuum: about 20 inches of Hg to about 29 inches of Hg (about 515 mm Hg to about 735 mm Hg). Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused chicken drum sticks prepared according to the above-described method of the present invention, has no substantial smoky aroma, has improved acceptably-mild smoky taste and has enhanced preservation at ordinary refrigeration temperature.

Example 30

The method as described above for the production of smoke-infused turkey breast is modified for the production of smoke-infused duck thighs. The procedure is controlled to be carried out as follows: Vacuum: about 20 inches of Hg to about 29 inches of Hg (about 515 mm Hg to about 735 mm Hg). Smoke in: smoke introduction for about 1 to about 10 seconds Vacuum pulse for about 5 to about 30 seconds Vacuum release for about 1 to about 10 seconds Number of cycles: 50 to about 400 cycles Chilled resting cycle: about 1 to about 6 hours at about 1° C. to about 6° C.

The smoke infused duck thighs prepared according to the above-described method of the present invention, has no substantial smoky aroma, has improved acceptably-mild smoky taste and has enhanced preservation at ordinary refrigeration temperature.

The method of aspect of this invention may be carried out with equally-effective results on all the poultry specifically-listed hereinabove.

Example 31

Cheeses may be smoke-infused with *Cannabis* compounds according to one embodiment of the method of the present invention. The smoke-infusing method on cheddar cheese according to an embodiment of this invention, is carried out as described below.

Pieces of the cheddar cheese to be smoke-infused are placed in desired proportions on trays within the interior of the vacuum vessel as previously defined in FIG. 2, FIG. 3, FIG. 4 and FIG. 5. The vacuum vessel is then sealed. The vacuum pump as previously defined is operated as previously defined to create a negative pressure within the vacuum-treating vessel of the order of about 26 inches of Hg to 29 inches of Hg (from about 670 mm of Hg to about 735 mm Hg), i.e., at or nearly at full vacuum. Smoke is generated by burning wood sawdust pellets which have about 50% *Cannabis* plant material content, and has an increased smoke content which has been provided by the above-described recycling, and which initially has a smoke/air mixture moisture content of about 10% to about 50%, by weight, is then admitted into the vacuum-treating vessel until equilibrium is reached. Smoke introduction is then ceased and substantially simultaneously vacuum is applied. The smoke infusion takes place at a suitable low temperature e.g., of about 4° C. for a time of about 2 to 20 seconds. The smoke which has not been perfused into the cheddar cheese to be smoke-infused is then removed. This sequence of method steps, i.e., introducing smoke into the vacuum-treating zone, and then removing the smoke is repeated about 50 to about 400 times, i.e., in pulsed sequences of smoke introduction stage/vacuum purging stage/vacuum release stage; which results in the efficient infusion of smoke into the cheddar cheese. This pulsed sequence of smoke introduction stage/vacuum purging stage/vacuum release stage is periodically repeated, as above noted, i.e., smoke introduction stage for about 1 to about 10 seconds, vacuum purging stage for about 5 to about 30 seconds and vacuum release stage for about 1 to about 10 seconds for about 50 to about 400 cycles. In order to remove the smoke-infused cheddar cheese from the vacuum vessel, fresh air is introduced to bring the vacuum vessel to atmospheric pressure.

The *Cannabis* and smoke-infused cheddar cheese is removed. An empirical test is performed to assess the odor and taste of the *Cannabis* and smoke-infused cheddar cheese.

Thus, the procedure is controlled to be carried out as follows: Vacuum: about 26 inches of Hg to about 29 inches of Hg (from about 670 mm of Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles The removed smoke-infused cheddar cheese is subjected to the additional essential step of a chilled resting cycle as previously described in the cold room at a temperature of about 2° C. to about 6° C. for a period of about 6 hours. Thus, the chilled resting cycle is about 1 to about 6 hours at about 2° C. to about 6° C.

The *Cannabis* and smoke-infused cheddar cheese which has been prepared by the smoke-infusion method of an aspect of the present invention as described above and which includes the above-described essential step of the chilled resting cycle as above specified, is again subjected to the empirical test to assess the odor and taste.

Example 32

Various red meats and poultry may be smoke-infused with *Cannabis* compounds according to an embodiment of the method of the present invention. The smoke-infusing method may be used with beef brisket in order to produce a marijuana-smoked beef jerky, which is carried out as described below.

Pieces of the brisket to be smoke-infused are placed in desired proportions on trays within the interior of the vacuum vessel as previously defined in FIG. 2, FIG. 3, FIG. 4 and FIG. 5. The vacuum vessel is then sealed. The vacuum pump as previously defined is operated as previously defined to create a negative pressure within the vacuum-treating vessel of the order of about 26 inches of Hg to 29 inches of Hg (from about 670 mm of Hg to about 735 mm Hg), i.e., at or nearly at full vacuum. Smoke is generated by burning wood sawdust pellets which have about 50% *Cannabis* plant material content, and has an increased smoke content which has been provided by the above-described recycling, and which initially has a smoke/air mixture moisture content of about 10% to about 50%, by weight, is then admitted into the vacuum-treating vessel until equilibrium is reached. Smoke introduction is then ceased and substantially simultaneously vacuum is applied. The smoke infusion takes place at a suitable low temperature e.g., of about 4° C. for a time of about 2 to 20 seconds. The smoke which has not been perfused into the beef brisket to be smoke-infused is then removed. This sequence of method steps, i.e., introducing smoke into the vacuum-treating zone, and then removing the smoke is repeated about 50 to about 400 times, i.e., in pulsed sequences of smoke introduction stage/vacuum purging stage/vacuum release stage; which results in the efficient infusion of smoke into the beef brisket. This pulsed sequence of smoke introduction stage/vacuum purging stage/vacuum release stage is periodically repeated, as above noted, i.e., smoke introduction stage for about 1 to about 10 seconds, vacuum purging stage for about 5 to about 30 seconds and vacuum release stage for about 1 to about 10 seconds for about 50 to about 400 cycles. In order to remove the smoke-infused beef brisket from the vacuum vessel, fresh air is introduced to bring the vacuum vessel to atmospheric pressure.

The *Cannabis* and smoke-infused beef brisket is removed. An empirical test is performed to assess the odor and taste of the *Cannabis* and smoke-infused beef brisket.

Thus, the procedure is controlled to be carried out as follows: Vacuum: about 26 inches of Hg to about 29 inches of Hg (from about 670 mm of Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles The removed smoke-infused beef brisket is subjected to the additional essential step of a chilled resting cycle as previously described in the cold room at a temperature of about 2° C. to about 6° C. for a period of about 6 hours. Thus, the chilled resting cycle is about 1 to about 6 hours at about 2° C. to about 6° C.

The *Cannabis* and smoke-infused beef brisket which has been prepared by the smoke-infusion method of an aspect of the present invention as described above and which includes the above-described essential step of the chilled resting cycle as above specified, is again subjected to the empirical test to assess the odor and taste. Additional steps may be taken to further remove moisture from the beef brisket in order to ensure its suitability as beef jerky if long term storage is desired.

Example 33

Various fish, crustaceans and other types of seafood may be smoke-infused with *Cannabis* compounds according to an embodiment of the method of the present invention. The smoke-infusing method may be used on lobster in order to produce a marijuana-smoked lobster, which is carried out as described below.

American or Canadian cold water clawed lobsters were separated from the shell by usual means, e.g., by the method described in U.S. Pat. No. 6,159,528 patented Dec. 12, 2000 by Gallant et al, (the entire contents of which are hereby incorporated by reference), which provided methods for separating the intact shell of hard-shelled crustaceans from the raw edible meat contained therein which is very strongly attached to the shells by specified freeze-thaw cycles. The so-separated meat is subjected to the method of the present invention under the method conditions previously described in detail.

Pieces of the separated meat of the lobster to be smoke-infused are placed in desired proportions on trays within the interior of the vacuum vessel as previously defined in FIG. 2, FIG. 3, FIG. 4 and FIG. 5. The vacuum vessel is then sealed. The vacuum pump as previously defined is operated as previously defined to create a negative pressure within the vacuum-treating vessel of the order of about 26 inches of Hg to 29 inches of Hg (from about 670 mm of Hg to about 735 mm Hg), i.e., at or nearly at full vacuum. Smoke is generated by burning wood sawdust pellets which have about 50% *Cannabis* plant material content, and has an increased smoke content which has been provided by the above-described recycling, and which initially has a smoke/air mixture moisture content of about 10% to about 50%, by weight, is then admitted into the vacuum-treating vessel until equilibrium is reached. Smoke introduction is then ceased and substantially simultaneously vacuum is applied. The smoke infusion takes place at a suitable low temperature e.g., of about 4° C. for a time of about 2 to 20 seconds. The smoke which has not been perfused into the lobster meat to be smoke-infused is then removed. This sequence of method steps, i.e., introducing smoke into the vacuum-treating zone, and then removing the smoke is repeated about 50 to about 400 times, i.e., in pulsed sequences of smoke introduction stage/vacuum purging stage/vacuum release stage; which results in the efficient infusion of smoke into the lobster meat. This pulsed sequence of smoke introduction stage/vacuum purging stage/vacuum release stage is periodically repeated, as above noted, i.e., smoke introduction stage for about 1 to about 10 seconds, vacuum purging stage for about 5 to about 30 seconds and vacuum release stage for about 1 to about 10 seconds for about 50 to about 400 cycles. In order to remove the smoke-infused lobster from the vacuum vessel, fresh air is introduced to bring the vacuum vessel to atmospheric pressure.

The *Cannabis* and smoke-infused lobster meat is removed. An empirical test is performed to assess the odor and taste of the *Cannabis* and smoke-infused lobster meat.

Thus, the procedure is controlled to be carried out as follows: Vacuum: about 26 inches of Hg to about 29 inches of Hg (from about 670 mm of Hg to about 735 mm Hg) Smoke in: smoke introduction for about 1 to about 10 seconds Vacuum pulse for about 5 to about 30 seconds Vacuum release for about 1 to about 10 seconds Number of cycles: 50 to about 400 cycles The removed smoke-infused lobster meat is subjected to the additional essential step of a chilled resting cycle as previously described in the cold room at a temperature of about 2° C. to about 6° C. for a period of about 6 hours. Thus, the chilled resting cycle is about 1 to about 6 hours at about 2° C. to about 6° C.

The *Cannabis* and smoke-infused lobster meat which has been prepared by the smoke-infusion method of an aspect of the present invention as described above and which includes the above-described essential step of the chilled resting cycle as above specified, is again subjected to the empirical test to assess the odor and taste.

While the above smoke infusion has been described for extracted lobster meat, it is equally applicable to the following lobster smoke infusions:

The lobster shell may be scored and the entire lobster may be subjected to the smoke infusion; i.e, below the lobster shell.

The lobster claws may be separated from the entire lobster, then scored and the scored lobster claws may be subjected to the smoke infusion; below the lobster claw shell.

The lobster tails may be separated from the entire lobster, then scored and the scored lobster tails may be subjected to the smoke infusion; below the lobster tail shell.

The whole lobster may be eviscerated and the whole eviscerated lobster may be subjected to the smoke infusion.

CONCLUSION

There are many commercial-advantages of carrying out the methods of aspects of the present invention. Such advantages include: such smoke-infused proteinaceous foods, e.g., cheeses, crustaceans, bivalve mollusks, gastropod mollusks, fish, meats and poultry prepared by the methods of the present invention are able to attain a maximized value in market places distant to their point of origin, where the perceived value of such smoke-infused proteinaceous foods, e.g., cheeses, crustaceans, bivalve mollusks, gastropod mollusks, fish, meats and poultry is highest and thus to attain higher levels of pricing than is traditionally available as commodity processors and thereby an enhanced ability to return more economic advantage to such smoke-infused proteinaceous foods, e.g., cheeses, crustaceans, bivalve mollusks, gastropod mollusks, fish, meats and poultry resource; such smoke-infused crustaceans, bivalve mollusks, gastropod mollusks, fish, meats and poultry processing communities are able to compete with and potentially displace sales of live such smoke-infused crustaceans, bivalve mollusks, gastropod mollusks, and fish and thereby reduce high costs of live (and frozen) shipping (often by air carriers) and in-transit mortalities (referred to as shrinkage) which is generally recognized within the industry often to exceed 8% in commercial supply chain situations; that the market place is able to receive a consistent and year-round supply of the such crustaceans, bivalve mollusks, gastropod mollusks and fish and thereby provide a year-round and consistent product offering to the customer base with reduced pricing volatility; the ability of the processors of such smoke-infused proteinaceous foods, e.g., cheeses, crustaceans, bivalve mollusks, gastropod mollusks, fish, meats and poultry to provide smoke-infused such smoke-infused proteinaceous foods, e.g., cheeses, crustaceans, bivalve mollusks, gastropod mollusks, fish, meats and poultry to the world market which can be produced on a mass processing scale and thereby supply mass market (both retail and food service) demands, which is a capacity that has not heretofore been achieved as methods for rapid and acceptable reconstitution of such smoke-infused proteinaceous foods, e.g., cheeses, crustaceans, bivalve mollusks, gastropod mollusks, fish, meats and poultry have not been developed; the methods provide for the removal of the meat of the smoke-infused crustaceans, bivalve mollusks, and gastropod mollusks from their shells, whether they are cooked from the frozen-thawed status or from smoke-infused frozen-thawed status from the shell with avoidance of meat adhesion to the shell material, which is particularly typically associated with cold water clawed lobsters that have been frozen from live status, and thereby, the end-user is able to consume the smoke-infused cold water clawed lobsters with satisfaction and user-friendliness which is necessarily associated with its relative high cost and value perception; and the marketplace is able to receive a consistent and year-round supply of the smoke-infused crustaceans, bivalve mollusks and gastropod mollusks and thereby to provide a year-round and consistent product offering to the customer base with reduced pricing volatility.

The claims, and the language used therein are to be understood in terms of the variants of the invention which have been described. They are not to be restricted to such variants, but are to be read as covering the full scope of the invention as is implicit within the invention and the disclosure that has been provided herein.

The invention claimed is:

1. A method for depositing *Cannabis*-derived compounds on the surface of smoke-infused cheese during the process of smoke infusing said cheese comprising the steps of:
   A. introducing cheese into an enclosable smoke-infusing zone;
   B. repeatedly cycling said enclosable smoke-infusing zone with a plurality of smoke-infusing cycles, each said smoke-infusing cycle comprising the steps of:
      a) converting said enclosable smoke-infusing zone into an enclosed smoke-infusing zone, and then pulling a vacuum on said enclosed smoke-infusing zone to convert said enclosed smoke-infusing zone to an enclosed vacuum smoke-infusing zone,
      b) flowing smoke containing *Cannabis*-derived compounds at atmospheric pressure, or at above atmospheric pressure from a smoke generation providing zone into said enclosed vacuum smoke-infusing zone, thereby substantially filling said enclosed vacuum smoke-infusing zone with said smoke, c) terminating said flow of said smoke into said enclosed vacuum smoke-infusing zone, d) providing a time for each flow of said smoke into said enclosed vacuum smoke-infusing zone in the range of between about 5 seconds and about 7 seconds C. repeating steps a-d between a range of about 100 to about 400 cycles to produce cheese which is smoke-infused;

D. releasing the vacuum in said enclosed vacuum smoke-infusing zone by admitting ambient pressure air into said enclosed vacuum smoke-infusing zone, whereby said enclosed vacuum smoke-infusing zone is brought to a state of ambient air pressure, and residual smoke remaining in said enclosed vacuum smoke-infusing zone is expelled from said enclosed vacuum smoke-infusing zone, E. withdrawing said smoke-infused cheese from said vacuum smoke-infusing zone, which is now in a state of ambient air pressure, and subjecting said withdrawn smoke-infused cheese to a chilled resting cycle in a cold zone, at a suitable low temperature of between about 0° C. to about 4° C. and for a suitable period of time between at least about 1-10 hours, thereby to provide smoke-infused cheese with *Cannabis*-derived compounds deposited on the surface of the cheese.

2. The method of claim 1, wherein said step of flowing said smoke from said smoke generation/providing zone into said vacuum smoke-infusing zone comprises:

i. providing a smoke holding/accumulation zone;

ii. introducing smoke from said smoke generation/providing zone into said smoke holding/accumulation zone; and iii. flowing said smoke from said smoke holding/accumulation zone into said vacuum smoke infusing zone thereby, to increase the concentration of smoke in said smoke holding/accumulation zone.

3. The method of claim 2, including the steps of, iv. recycling smoke from said smoke holding/accumulation zone back into a conventional air inlet to said smoke generation/providing zone, thereby to provide concentrated smoke in said smoke holding/accumulation zone; and v. introducing said concentrated smoke from said smoke holding/accumulation zone into said vacuum smoke-infusing zone, thereby to increases the infusion of said smoke into said cheese.

4. The method of claim 3 wherein residual smoke remaining in said vacuum smoke-infusing zone is expelled by being flushed into a connectable, residual smoke retention zone, and sealing said connectable smoke retention zone, and thus trapping said residual smoke in said connectable smoke retention zone, whereby said trapped residual smoke within said residual smoke retention zone is capable of being re-introduced into said vacuum smoke-infusing zone.

5. The method of claim 3, wherein a negative pressure in said vacuum smoke-infusing zone is in the range of about 22 inches of Hg to 29 inches of Hg.

6. The method of claim 5, wherein said negative pressure in said vacuum smoke-infusing zone is about 29 inches of Hg.

7. The method of claim 1, wherein the flow of said smoke is by smoke injection pulses.

8. The method of claim 1, wherein said method is carried out at ambient room temperature.

9. The method of claim 1, wherein said smoke in step b is at atmospheric pressure.

10. The method of claim 1, wherein said smoke is produced by burning *Cannabis* plant material.

11. The method of claim 10 wherein the *Cannabis* plant material has been combined with another fuel.

12. The method of claim 11, wherein said fuel is one or more fuels selected from the group consisting of wood, coconut fibre, or peat.

13. The method of claim 11, wherein said *Cannabis* plant material is combined in a measured ratio with said fuel, wherein said *Cannabis* plant material comprises about 30 to about 70 percent of the combination, and said fuel comprises the remaining about 70 to about 30 percent of the combination, such that the combination of *Cannabis* plant material and fuel add up to 100 percent.

14. The method of claim 1, wherein said smoke has a moisture content of about 10% to about 50% by weight.

15. The method of claim 14, wherein said smoke has a moisture content of about 35% by weight.

16. The method of claim 1, wherein the smoke has a concentration of up to about 50% by weight.

17. The method of claim 16, wherein the concentration of smoke is about 35% by weight.

18. The method of claim 1, wherein said suitable low temperature of said chilled resting cycle in a dry cold zone is between about 2° C. and about 4° C.

19. The method of claim 18, wherein said suitable temperature for said chilled resting cycle is about 3° C.

20. The method of claim 1, wherein said chilled resting cycle is performed for between about 6 and about 10 hours.

21. The method of claim 20, wherein said chilled resting cycle is performed for about 8 hours.

22. The method of claim 1, wherein said cheese is one of the following cheeses: Acapella, Banan, Bergere Blue, Brick, Capriole, Cheddar, Cojack, Colby, Colby-Jack, Cold Pack, Cougar Gold, Crowley, Chevre, Farmer, Fresh Jack, Blue Cow, Fog, Goatster, Monterey Jack, Muenster, Marble Cheddar, Mascarpone, Pepper Jack, Provel Swiss, Gruyere, Fontina, Lunenburg, Colija, Regganete, Sarde, Beauvoords, Brussels Kaas, Bruges, Herve, Limburger, Maredsous, Passendale, Plateau de Herve, Postel, Prince-jean, Remedou, Rubens, Caerphilly, Cheshire, Derby, Double Gloucester, Lancashire, Red Lancashire, Red Windsor, Stilton, Dorset Blue Vinney, Hertford Hop, Leafield, Lincolnshire Poacher, Llanglofan, Farmhouse, Malvern, Penryn, Pencarreg, Sage Derby, Shropshire Blue, Basing, Bath, Beenleigh Blue, Berkswell, Bosworth, Buffalo, Button (Innes), Buxton Blue, Capricorn Goat, Cerney, Coquetdale, Cornish Pepper, Clotherstone, Coverdale, Curworthy, Denhany, Dorset Drum, Devon Blue, Devon Garland, Double Worcester, Dudleswell, Emlett, Exmoor Blue, Finn, Flower Marie, Friesla, Gloucester, Golden Cross, Gospel Green, Harboume Blue, Herriot Farmhouse, Lancashire, Leicester, Little Ridings, Lodiswell Avondale, Longhorn, Menallack Farmhouse, Northumberland, Olde York, Oxford Blue, Red Leicester, Sharpam, Somerset Blue, Spenwood, Staffordshire, Stinking Bishop, Sussex, Slipcote, Swandale, Tala, Tymsboro, Tyning, Vulscombe, Waterloo, Wellington, Wensleydale, White Stilton, Wigmore, Yorkshire Blue Havarti, Mozzarella, Parmesan, Raclette, Oka, Castello, Cream Danablu, Danbo, Esrom, Fynbo, Tilsit-Havarti, Maribo, Mycella, Saga, Somsoe, Abbaye de Belloc, Abbaye de Citeau, Abbaye de Mont des Cats, Abundance, Affidelice au Chablis, Aisy Cendre, Ambert, Amid du Chambertin, Anneau du Vie-bilh, Ardi Gasna, Aromes au Gene de Marc, Aubisque Pyrenees, Autun, Babybel, Baguette Lyonnaise, Banon, Beaufort, Bethmale des Pyrenees, Blue Auverbne, Blue de Gex, Blue de Laqueuille, Blue de Septmongel, Blue de Termignon Alpage, Blue des Causes, Blue de Termignon, Bougon, Boule du Royes, Boulette d'Avesnes, Boursault, Boursin, Bouyssou, Brebis du Lavort, Brebis du Loehois, Brebis du Puyfaucon, Bres Bleu, Brie, Brie du Poivre, Brie de Meaux, Brie de Melon, Brillat-Savarin, Brin, Brind'd Amour, Briquette de Brebis, Briquette du Parez, Broccio, Broccio Demi-Affine, Brouse du Rove, Buchette d'Anjou, Butte, Cabecou, Cachaille, Calenzana, Camembert, Cantle, Caprice des Dieux, Carre del'Est, Cathelain, Cendre d'Olivet, Chabichou, Chabichou du Poitou, Chabis de Gatins, Chaource, Charolais, Chaumes, Chevrotin des Aravis, Civray, Couer de Camembert au Calvados, Couer de Chevres, Compte, Coulommiers, Crayeux, Crotin de Chavignol, Cure Nantais, Dauphin, Delices des Fiouves, Dreux a la Feuille, Emental Grand Cru, Epoisses de Bourgogne, Esbareich, Etorki, Explorateur, Pigue, Filetta, fin-de-Siecle, Fleur du Maquis, Fondant de Brebis, Fougerus, Fourme d'Ambert, Fourme de Haute Loire, Forme de Montbrison, Frinault, Fromage a Racklette, Fromage Corse, Fromage de Montagne de Savois, Fromasge Frais, Galette du Paluder, Galette Lyonais, Gaperon a l'Ail, Gastanberra, Goutu, Geand Vatel, Gratarond'Areches, Grate-Paille, Grueilh, Gris de Lille, Guerbigny, Ile d'Yeu, L'Aveyronnais, L'Ecir de L'aubrae, La Taupiniere, La Vache Qui Rit, Languiole, Langres, Laruns, La Brin, Le Fium Orbo, La Lacandou, Le Roule, Linguit Saint Bousquet d'Orb, Livarot, Lou Palou, Lou Poirvre, Lyonais, Macconais, Mamirole, Margoyin, Maroilles, Mascares, Matocq, Meyyon (Cancoillotte), Mimolette, Mixte, Mont d'Or Lyonais, Morbier, Morbier Cru Demontagner, Mothais, Munster, Murol, Nantais, Neufchatel, Niolo, Olivet au Foin, Olivet Blue, Olivet Cendre, Ossau Fermier, Ossau-lraty, P'tit Berrichon, Palet de Babligny, Pas de l'Escalette, Pate de Fromager, Patefine Fort, Pave d'Affinois, Pave d'aAuge, Pave de Chirac, Pave du Berry, Pelardon des Corbieres, Perail de Brebis, Petit Morin, Petir Pardou, Petit-Suisse, Picodon de Chevre, Pithtviers au Foin, Poivre d'Ane, Pont l'Eveque, Port Salut, Pouligny Saint-Pierre, Poorly, Pyramide, Quatre-Vents, Quercy Petit, Raclette, Reblochon, Regal de la Dombes, Rigotte, Rocamadour, Rollot, Romans l'Art Dieu, Roquefort, Roule, Rouleau de Beaulieu, Sustin, Saint Maure, Saint-Marcellin, Saint-Nectaire, Saint-Paulin, Salers, Sancerre, Selles Sur Cher, Soumaintrain, Sourire, Tamie, Taupiniere, Tome Brulee, Tome d'Abondance, Tome de Romans, Tome de Savoie, Tome des Chouans, Tomes, Tommes l'Aubier, Tourmalet, Trappe (Veritable), Trios Comes de Vendee, Trou du Cru, Tuffe, Valernay, Venaco, Vend6mois, Vieux Corse Vignette, Lappi Finlandia, Algauer Emmentaler, Bavarian Bierkasse, Bergader, Bruder Basil, Butterkasse, Cambazola, Doppelrhamstufel, Edelpilz, Jermi Tortes, Klosterkasse, Quark, Tilsit Weichkasse, Boeren, Edam, Friesian, Gouda, Kemhem, Leerdammer, Leyden, Maasdam, Mimolette Commissickaas, Ardrham, Baylough, Blarney, Blue Tathgore, Cashel Blue, Coolea, Corleggy Cooleney, Corleggy, Crogham, Doolin, Dubliner, Dunbarra, Durus, Gabriel, Gubbeen, Knockalara, Lavistown, MineGabhar, Oral, Asiago, Bel Paese, Bocconcini, Bra, Caciocavallo, Caciotta, Canestrato, Casciotta di Urbano, Castelmagno, Cerescenza, Dolcette, Fiore Sardo, Fontal, Fontina Val d'Aosta, Fontina, Formagio di Capra, Mozzarella, Ricotta, Truffles Gorgonzola, Grana, Gran Padano, Ilboschetto al Tartufo, Mascarpone, Mascarpone Torta, Montasio, Mozzarella, Mozzarella di Bufala, Mozzarella, Rolla, Parmesan, Provolone, Ricotta, Romano, Pannerone, Parmesan (Parmigiano), Parmigiano Reggiano, Recorino, Pecorino, in Walnut Leaves, Pecorino Romano, Pressato, Provolone, Quartirolo Lombardaro, Ragusano, Raschera, Ricotta, Ricotta Salata, Romano, Scamorza, Sottocenare al Tartufo, Taleggio, Toma, Toscanello, Ubriaco, Zanetti Gran Padano, Zanrtti Parmigiano Reggino, Airdale, Barry's Bay Cheddar, Evansdale Farmhouse, Four Herb Gouda, Hipiiti, Jubilee Blue, Kikorangi, Mahoe Meyer Vintage gouda, Port Nicholson, Waimata Farmhouse Blue Whitestone Farmhouse, Gamalost, Geitost, Jarlsberg Norvegia, Galost, Nikkelost Riddler Koldemer, Labelsta, Marski, Pomski Pudlasker, Kkurprank, Afuega'l Pitu, Aragon, Burgos, Cabralescastellano, Castigliano, Cuajada, Flor de Guia, Garrotsa, Iberico, Idiazabel, Manchego, Menonita, Penamellera, Picos de Europa, Queso de Murcia, Queso del Montsec, Queso del Tietar, Queso Iberico, Queso Majorero, Requeson, San Simon, Selva, Tetilla, Torta Delcesar, Tronchon, Tupi, Ulloa Zamorano, Swedish Farmers, Swedish Fontina, Adelost, Graddost, Greve, Herrgardost, Hushhallsost, Messot, Prastost, Saaland Pfarr, Sveciaost Vasterbottenost, Appenzell, Emmenthal, Fribourgeouse, Neufchatel, Piora, Royal Tilsit, Saanenkaese, Sap Sago, Sbrinz, Schabzeiger, Tete de Moine and Vacherin.

23. The method of claim 22, wherein said cheese is Cheddar, Colby, Swiss, Gruyere, Brick, Farmer's, Havarti, Mozzarella, Parmesan, Havarti, Edam, Gouda, Emmenthal, Romano, Dubliner, or Jarlsberg.

24. A method of preparing a sealed portion of smoke-infused cheese which comprises carrying out the method of claim 1 and, including a further step selected from the group consisting of:
   a) vacuum sealing said smoke-infused cheese in a sealable pouch or package;
   b) shrink-wrapping said smoke-infused cheese in a shrink-wrap pouch or package;
   c) wax coating said smoke-infused cheese in a wax suitable for cheese waxing.

25. The method of claim 24, wherein the cheese is Cheddar, Colby, Swiss, Gruyere, Brick, Farmer's, Havarti, Mozzarella, Parmesan, Havarti, Edam, Gouda, Emmenthal, Romano, Dubliner, or Jarlsberg.

* * * * *